United States Patent [19]

Leone-Bay et al.

[11] Patent Number: 5,629,020
[45] Date of Patent: May 13, 1997

[54] MODIFIED AMINO ACIDS FOR DRUG DELIVERY

[75] Inventors: Andrea Leone-Bay, Ridgefield, Conn.; Nai F. Wang, Long Island City, N.Y.

[73] Assignee: Emisphere Technologies, Inc., Hawthorne, N.Y.

[21] Appl. No.: 231,622

[22] Filed: Apr. 22, 1994

[51] Int. Cl.$^6$ .............................. A61K 9/14; A61K 9/48; A61K 9/20
[52] U.S. Cl. .................. 424/489; 424/451; 424/464; 514/553; 514/561
[58] Field of Search ................ 424/464, 489, 424/451, 477, 491, 499, 490; 514/561, 553

[56] References Cited

U.S. PATENT DOCUMENTS

| | | | |
|---|---|---|---|
| Re. 24,899 | 11/1960 | Green | 428/402.2 |
| 2,671,451 | 3/1954 | Bolger | 128/260 |
| 2,862,918 | 12/1956 | Meyer et al. | 260/123.5 |
| 2,868,740 | 1/1959 | Luce | 260/8 |
| 2,971,916 | 2/1961 | Schleicher et al. | 252/62.5 |
| 3,016,308 | 1/1962 | Macaulay | 117/36.7 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima | 99/145 |
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/87 |
| 3,567,650 | 3/1971 | Bakan | 252/316 |
| 3,574,832 | 4/1971 | Engel et al. | 424/183 |
| 3,576,758 | 4/1971 | Emrick | 253/316 |
| 3,725,113 | 4/1973 | Chang | 117/82 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |

(List continued on next page.)

FOREIGN PATENT DOCUMENTS

| | | |
|---|---|---|
| 1077842 | 8/1976 | Canada . |
| 0000667A1 | 2/1979 | European Pat. Off. . |
| 0036145A1 | 9/1981 | European Pat. Off. ....... A61K 31/62 |
| 0068314 | 1/1983 | European Pat. Off. . |
| 0105804 | 4/1984 | European Pat. Off. . |
| 0130162A2 | 1/1985 | European Pat. Off. . |
| 0170540A1 | 2/1986 | European Pat. Off. . |
| 0342054A2 | 11/1989 | European Pat. Off. . |
| 0342056A2 | 11/1989 | European Pat. Off. . |
| 0365183 | 4/1990 | European Pat. Off. ...... C07C 311/21 |

(List continued on next page.)

OTHER PUBLICATIONS

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al., (1989), *Thrombosis Research* 56:119–124.

Gelb, R., et al (1983), *Life Sciences* 33(1):83–85.

(List continued on next page.)

*Primary Examiner*—Gollamudi S. Kishore
*Attorney, Agent, or Firm*—Darby & Darby

[57] ABSTRACT

The present invention relates to an oral delivery system, and in particular to modified amino acids or peptides for use as a delivery system of sensitive agents such as bioactive peptides. The modified amino acids or peptides can form non-covalent mixtures or microspheres with active biological agents. These mixtures or microspheres are suitable for oral administration of biologically active agents to animals. Methods for the preparation of such amino acids and peptides are also disclosed.

29 Claims, 17 Drawing Sheets

Dosage
- ▲ - cycloheptanoyl-Leu + (400 μg/kg) + (10μg) sCT
- ■ - 2-methylcyclohexanoyl-Leu + (400 μg/kg) + (10μg) sCT
- ● - cyclohexanoyl-Leu (400 μg/kg) + (10μg) sCT

5,629,020

U.S. PATENT DOCUMENTS

| Number | Date | Inventor | Class |
|---|---|---|---|
| 3,937,668 | 2/1976 | Zolle | 424/1.29 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 514/255 |
| 4,035,507 | 7/1977 | Bodor et al. | 424/311 |
| 4,048,268 | 9/1977 | Ludwig | 264/15 |
| 4,147,767 | 4/1979 | Yapel | 424/499 |
| 4,183,849 | 1/1980 | Hansen | 530/305 |
| 4,217,370 | 8/1980 | Rawlings et al. | 426/98 |
| 4,289,759 | 9/1981 | Heavner et al. | 514/11 |
| 4,348,384 | 9/1982 | Horikoshi et al. | 424/450 |
| 4,351,337 | 9/1982 | Sidman | 424/425 |
| 4,352,883 | 10/1982 | Lim | 435/178 |
| 4,354,588 | 10/1982 | Widder et al. | 600/12 |
| 4,357,259 | 11/1982 | Senyei et al. | 264/43 |
| 4,442,090 | 4/1984 | Kakeya et al. | 424/178 |
| 4,446,138 | 5/1984 | Pack | 514/255.2 |
| 4,450,150 | 5/1984 | Sidman | 424/424 |
| 4,462,991 | 7/1984 | Higuchi et al. | 424/177 |
| 4,483,807 | 11/1984 | Asano | 264/460 |
| 4,492,684 | 1/1985 | Goosen et al. | 424/486 |
| 4,608,278 | 8/1986 | Frank | 427/213.35 |
| 4,666,641 | 5/1987 | Fickat et al. | 264/43 |
| 4,671,954 | 6/1987 | Goldberg | 424/137 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/68.1 |
| 4,757,066 | 7/1988 | Shiokari | 514/210 |
| 4,835,312 | 5/1989 | Itoh et al. | 564/205 |
| 4,837,381 | 6/1989 | Steber et al. | 424/502 |
| 4,873,087 | 10/1989 | Morishita | 426/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,919,939 | 4/1990 | Baker | 424/493 |
| 4,925,673 | 5/1990 | Steiner | 540/538 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 514/2 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 514/255 |
| 5,250,236 | 10/1993 | Gasco | 264/4.4 |
| 5,271,961 | 12/1993 | Mathiowitz et al. | 427/213.31 |
| 5,278,148 | 1/1994 | Branca | 514/19 |
| 5,284,133 | 2/1994 | Boyes et al. | 424/501 |
| 5,310,535 | 5/1994 | Kruper et al. | 424/153 |
| 5,352,461 | 10/1994 | Feldstein et al. | 424/493 |
| 5,389,379 | 2/1995 | Dirix et al. | 424/451 |
| 5,418,010 | 5/1995 | Janda et al. | 427/213.31 |
| 5,451,410 | 9/1995 | Milstein et al. | 424/490 |

FOREIGN PATENT DOCUMENTS

| | | | |
|---|---|---|---|
| 0366277 | 5/1990 | European Pat. Off. | |
| 0418642 | 3/1991 | European Pat. Off. | |
| 0448057 | 9/1991 | European Pat. Off. | |
| 0452161 | 10/1991 | European Pat. Off. | |
| 0459795 | 12/1991 | European Pat. Off. | |
| 0467389 | 1/1992 | European Pat. Off. | |
| 0490549A1 | 6/1992 | European Pat. Off. | A61K 47/12 |
| 0517211A1 | 9/1992 | European Pat. Off. | A16K 47/12 |
| 0616799A1 | 9/1994 | European Pat. Off. | A61K 7/00 |
| 1351358 | 3/1964 | France | |
| 1468601 | 2/1967 | France | |
| 2133926 | 12/1972 | France | |
| 2326934 | 5/1977 | France | |
| 2565102 | 12/1985 | France | |
| 2424169 | 12/1974 | Germany | |
| 3202255 | 10/1982 | Germany | |
| 3612102 | 10/1986 | Germany | |
| 71258/2 | 12/1987 | Israel | |
| 48-24246 | 3/1973 | Japan | |
| 56-68612 | 6/1981 | Japan | A61K 31/19 |
| 58-35111 | 3/1983 | Japan | |
| 280826 | 12/1964 | Netherlands | |
| 280825 | 12/1964 | Netherlands | |
| 146698 | 11/1982 | Norway | A61K 37/26 |
| 929401 | 6/1963 | United Kingdom | |
| 1075952 | 8/1967 | United Kingdom | |
| 1236885 | 6/1971 | United Kingdom | |
| 1567763 | 5/1980 | United Kingdom | |
| 2095994 | 10/1982 | United Kingdom | |
| WO85/00105 | 1/1985 | WIPO | |
| WO85/00110 | 1/1985 | WIPO | |
| WO85/02772 | 7/1985 | WIPO | |
| WO87/04076 | 7/1987 | WIPO | |
| WO88/01213 | 2/1988 | WIPO | |
| WO92/19263 | 12/1992 | WIPO | A61K 39/00 |
| WO93/18754 | 9/1993 | WIPO | A61K 9/16 |
| WO93/25583 | 12/1993 | WIPO | C07K 15/00 |
| WO94/14420 | 7/1994 | WIPO | A61K 9/16 |
| WO94/18997 | 9/1994 | WIPO | A61K 31/00 |
| WO94/21234 | 9/1994 | WIPO | A61K 7/00 |
| WO94/18950 | 9/1994 | WIPO | A61K 9/127 |
| WO94/24291 | 10/1994 | WIPO | A61K 39/015 |
| WO94/23767 | 10/1994 | WIPO | A61K 9/16 |
| WO94/23702 | 10/1994 | WIPO | A61K 9/16 |
| WO94/28878 | 12/1994 | WIPO | A61K 9/14 |
| WO95/11690 | 5/1995 | WIPO | A61K 37/00 |

OTHER PUBLICATIONS

Watterberg et al. (1988), *Pediatric Research*, vol. 23, No. 4, part 2, p. 570A, col. 1, abstract No. 2209.

Bernstein (1985), *Chest* 87(1):68S–73S.

Damage et al. (1988), *Diabetes* 37:246–251.

*Chemical Abstracts*:83 184358k, (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Hass, S. et al., "Assessment Of Stability Of Proteinoid Microspheres", *Proceed. Intern. Symp. Control. Rel. Bioact. Mater.*, 20 (1993), Controlled Release Society, Inc.

X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".

Yen, H.-R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at "*IBC Rational Drug Design Conference*", San Diego, Calif.—Dec. 1994.

Bergeron, Raymond J. et al., *J. Am. Chem. Soc.* 1994, 116,8479–8484 "Macromolecular Self–Assembly of Diketopiperazine Tetrapeptides".

Leone–Bay et al., Presented at "*Winter Conference on Medicinal and Bioorganic Chemistry*" Steamboat Springs, Colorado—Feb. 1995 Microsphere Formation and Drug Delivery in a Series of Derivatized Amino Acids.

Santigo et al., *Pharm. Res.* 11: 1994, p. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery Using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts*. AAPS Annual Meeting, San Antonia, TX, Nov. 15–19, 1993.

Santiago et al. "Initial Studies In The Asessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres"*Proceed. Intern. Symp. Control. Rel. Bioact. Mater.*, 19 (1992), Controlled Release Society, Inc., pp. 116–117.

Santiago et al. "Proteinoid Microspheres For The Oral Delivery of Heparin" *Proceed. Intern. Symp. Control. Rel. Bioact. Mater.*, 19 (1992), Controled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.*, 19 (1992), Controlled Release Society, Inc. pp. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

AAPS 6TH Ann. Meeting and Expo., "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug–loaded Proteinoid Microsphere Formulation during Freeze–drying" *Journal of Drug Targetting*, 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–39 "Physical barriers to drug delivery in tumors".

V. Hird et al, Genes and Cancer, edited by Desmond Carney & Karol Sikora, pp. 183–189, "Immunotherapy with Monoclonal Antibodies".

Michael E. Osband et al., Immunology Today, vol. 11, No. 6 1990, pp. 93–95, "Problems in the investigational study and clinical use of cancer immunotherapy".

Tibtech Feb. 1993 vol. 11, pp. 42–44 "Therapeutic antibodies—the coming of age".

Thomas A. Waldmann, Articles Jun. 21, 1991, pp. 1657–1662, "Monoclonal Antibodies in Diagnosis and Therapy".

Airaudo, C.B. et al. (1987) *Journal of Food Science*, vol. 52(6), pp. 1750–1752.

Andini, S. et al. (1975) *Origins of Life*, vol. 6, pp. 147–153.

Brooke, S. 1 et al. (1977) *BioSystems*, vol. 9, pp. 1–22.

Chen et al. (1975) "Evidence for Hemiacetal Formation", *Biochemistry*, vol. 18, No. 5, pp. 921–925.

Davis et al. (1983) "Leucinal Inhibits . . . ", *Pharmacology Biochemistry Behavior*, vol. 19, pp. 791–794.

Dose, K. (1974) *Origins of Life*, vol. 5, pp. 239–252.

Fasman et al. (1964) *Biochemistry*, vol. 3, No. 11, pp. 1665–1674.

Fox, S.W. et al. (1976) *BioSystems*, vol. 8, pp. 40–44.

Fox, S.W. et al., *Molecular Evolution and the Origin of Life*, Maxel Decker, New York (1977).

Fox, S.W. et al. (1968) *Biochim. Biophys. Acta*, vol. 160, pp. 246–249.

Fox, S.W. (1976) *Origins of Life*, vol. 7, pp. 49–68.

Fox, S.W. (1980) *Naturwissenschaften*, vol. 67, pp. 378–383.

Fox, S.W. et al. (1960) *Archives of Biochemistry and Biophysics*, vol. 86, pp. 281–285.

Fox, S.W. et al. (1974) *Origins of Life*, vol. 5, pp. 227–237.

Fox, S.W. (1984) *Origins of Life*, vol. 14, pp. 485–488.

Gol'dovskii, A.M. (1978) *Zhurnal Evolyutsionnoi Biokhimii i Fiziologii*, vol. 14(6), pp. 517–519.

Gurrieri, S. et al. (1973) *Thermochimica Acta*, vol. 7, pp. 231–239.

Harada, K. et al. (1979) *BioSystems*, vol. 11, pp. 47–53.

Harada et al., (1960) *Archives of Biochemistry and Biophysics*, vol. 86, pp. 274–280.

Hare (1970) *Etude Centique De La Polycondensation Thermique D'$_\chi$-Amino Acides*, vol. 45, pp. 330–339.

Heinrich, M.R. et al. (1969) *Archives of Biochemistry and Biophysics*, vol. 130, pp. 441–448.

Heinz, B. et al. (1981) *BioSystems*, vol. 14, pp. 33–40.

Hennon, G. et al. (1975) *Biochimie*, vol. 57, pp. 1395–1396.

Hsu, L.L. et al. (1976) *BioSystems*, vol. 8, pp. 89–101.

Hsu, L.L. et al. (1971) *Currents in Modern Biology*, vol. 4, pp. 12–25.

Ishima, Y. et al. (1981), *BioSystems*, vol. 14, pp. 243–251.

Jackson et al. (1991) "Pharmacological . . . ", *J. Pharm. & Exp. Thera.*, vol. 261, No. 1, pp. 546–552.

Jungck, J.R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. 516–517.
Krampitz, G. et al. (1968) *Naturwissenschaften*, pp. 345 and 346.
Krampitz, G. et al. (1966) *Naturwissenschaften*, pp. 7 and 8.
Lacey, Jr., J.C. et al. (1979) *BioSystems*, vol. 11, pp. 9–17.
Lacey, Jr., J.C. et al. (1979) *BioSystems*, vol. 11, pp. 1–7.
Martinez Luque–Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W.W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V.J.A. (1984) *Origins of Life*, vol. 14, pp. 513–533.
Olafsson, P.G. et al. (1971) *Polymer Letters*, vol. 9, pp. 521–528.
Phillips, R.D. et al. (1974) *Int. J. Peptide Res.*, vol. 6, pp. 309–319.
Przybylski, A.T. et al. (1982) *Die Naturwissenschaften*, vol. 69, pp. 561–563.
Przybylski, A.T. et al. (1984) *Applied Biochemistry and Biotechnology*, vol. 10, pp. 301–307.
Przybylski, A.T. (1985) *BioSystems*, vol. 17, pp. 281–288.
Rohlfing, D.L. (1975) *Origins of Life*, vol. 6, pp. 203–209.
Rohlfing, D.L. (1970) *Science*, vol. 169, pp. 998–1000.
Rohlfing, D.L. (1967) *Archives of Biochemistry and Biophysics*, vol. 118, pp. 468–474.
Rohlfing, D.L. et al. *Catalytic Activities of Thermal Polyanhydro–α–Amino Acids*, pp. 373–418.
Rohlfing, D.L. et al. (1976) *BioSystems*, vol. 8, pp. 139–145.
Ryan, J.W. et al. (1973) *BioSystems*, vol. 5, pp. 115–118.
Saunders, M.A. et al. (1974) *BioSystems*, vol. 6, pp. 81–92.
Snyder, W.D. et al. (1975) *BioSystems*, vol. 7, pp. 222–229.
Sokol, P.E. (1974) *Journal of the American Oil Chemists' Society*, vol. 52, pp. 101–102.
Tschager et al. (1989) *Milchwirtschaftliche Berichte*, vol. 95, pp. 79–83.
Vaughan, G. et al. (1987) *BioSystems*, vol. 20, pp. 219–223.
Vol'kenshtein, M.V. (1989) *Molekulyarnaya Biologiya*, vol. 23(1), pp. 23–37.
Waehneldt, T.V. et al. (1968) *Biochim. Biophys. Acta*, vol. 160, pp. 239–245.
Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.
Zulaski et al. (1983) "New Carboxyalkyl Inhibitors of Brain Enkenphalinase", *J. Med. Chem.*, 26, pp. 60–65.
(1985) *Chemical Abstracts*, vol. No. 105(1), Abstract No. 12027p.
(1985) *Chemical Abstracts*, vol. No. 102(6), Abstract No. 50870d.
Chemicla Abstract, vol. 80(5) Abst. 52392a.
Bergeron, Raymond J., et al. (1994) "Macromolecular Self-Assembly of Diketopiperazine Tetrapeptides", *Journal of the American Chemical Society*, vol. 116, pp. 8479–8484.
Bergeron, Raymond J., et al. (1993) "A Comparative Study of the Iron–Clearing Properties of Desferrithiocin Analogues With Desferrioxamine B in a *Cebus* Monkey Model", *Blood*, vol. 81, No. 8 pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.
Bergeron, Raymond J., et al. (1991) "Evaluation of Desferrithiocin and Ifs Synthetic Analogs as Orally Effective Iron Chelators", *Journal of Medicinal Chemistry*, vol. 34, No. 7, pp. 2072–2078.
Bergeron, Raymond et al., "A Comparative Evaluation of Iron Clearance Models", *Annals New York Academy of Sciences*, pp. 278–393.

Dosage
- ▲ - cycloheptanoyl-Leu + (400 μg/kg) + (10μg) sCT
- ■ - 2-methylcyclohexanoyl-Leu + (400 μg/kg) + (10μg) sCT
- ● - cyclohexanoyl-Leu (400 μg/kg) + (10μg) sCT

- ■ - cyclohexanoyl-Arg (400 mg/kg) + sCT (10 μg/kg)
- ● - cyclopentanoyl-Arg (400 mg/kg) + sCT (10 μg/kg)
- ▲ - cyclohexanoyl-Leu (400 μg/kg) + sCT (10 μg/kg)
- ▼ - cyclohexanoyl-Phg (400 mg/kg) + sCT (10 μg/kg)

- ● - cyclohexanoyl-Arg (266 mg/kg), cyclohexanoyl-Leu (266 mg/kg) & cyclohexanoyl-Tyr (266 mg/kg) + sCT (10 μg/kg)

- ■ - cyclohexanoyl-Leu (400 mg/kg) + sCT (3 mg/kg)
- ● - cyclohexanoyl-Gly (400 mg/kg) + sCT (3 mg/kg)
- ▼ - cyclopropanoyl-Leu (400 mg/kg) + sCT (3 mg/kg)

- ■ - N-cyclohexanoyl-(L)-Leucine (400 mg/kg) + sCT (3 ug/kg)
- ● - N-cyclohexanoyl-(L)-Leucine (400 mg/kg) + sCT (10 mg/kg)

DOSE RESPONSE: HEPARIN SPHERES

■ - Cyclohexanoyl-Leu (300 mg/kg) + Hep (25 mg/kg)
● - Cyclohexanoyl-Leu (300 mg/kg) + Hep (50 mg/kg)

- ■ - Cyclohexanoyl-Leu (600 mg/kg) + Hep (50 mg/kg)
- ● - Cyclohexanoyl-Leu (600 mg/kg) + Hep (100 mg/kg)

- ■ - Cyclohexanoyl-Arg. (100 mg/kg) + Hep (100 mg/kg)
- ● - Cyclohexanoyl-Arg. (600 mg/kg) + Hep (100 mg/kg)

Hep dosage = 100 mg/kg

Rats dosed ID, heparin spheres

- ● - Cyclohexanoyl-Leu (300 mg/kg) + Hep (25 mg/kg)
- ■ - Hep (25 mg/kg)

- ● - Hep control (50 mg/kg)
- ■ - Cyclohexanoyl-Leu (150 mg/kg) Empty spheres dosed 1/2 hr. before heparin (50 mg/kg)
- ▲ - Cyclohexanoyl-Leu (150 mg/kg) Hep (50 mg/kg)

Cyclohexanoyl-Leu (30 mg/kg) + LMWH (8000 IU/kg)

- ■ - cyclohexanoyl-Leu (300 mg/kg) + LMWH (2000 mg/kg)
- ● - cyclohexanoyl-Leu (300 mg/kg) + LMWH (200 mg/kg)
- ▲ - LMWH (200 IU/kg) subcutaneous dosage

- ■ - DSCG (50 mg/kg) $H_2O$: pH 7.2)
- ● - DSCG (50 mg/kg CA: pH 3.7)
- ▲ - Cyclohexanoyl-Leu 400 mg/kg + DSCG (50 mg/kg CA: pH 7.1)
- ▼ - Cyclopropanoyl-Leu 400 mg/kg + DSCG (50 mg/kg CA: pH 4.6)

- ● - Cyclohexanoyl-Phg (800 mg/kg) + Interferon 2ab (1 mg/kg)
- ■ - Cyclohexanoyl-Arg (800 mg/kg) + Interferon 2ab (1 mg/kg)

- ■ - Cyclohexanoyl-Phg (800 mg/kg) + Interferon 2ab (1 mg/kg)
- ● - Cyclohexanoyl-Arg (800 mg/kg) + Interferon 2ab (1 mg/kg)

Carrier Cyclohexanoyl Phg (800 mg/kg)

- ■ - 1.0 mg/kg rhIFN
- ● - 0.5 mg/kg rhIFN
- ▲ - 0.25 mg/kg rhIFN

MODIFIED AMINO ACIDS FOR DRUG DELIVERY

The present invention relates to compositions suitable for drug delivery, and in particular to compositions in which modified amino acids or peptides are used as carriers for biologically active agents including, but not limited, to bioactive peptides and the like. The modified amino acids or peptides can form non-covalent mixtures or microspheres with biologically-active agents and are suitable for oral administration to animals. Methods for the preparation and for the administration of such compositions are also disclosed.

BACKGROUND OF THE INVENTION

Conventional means for delivering biologically-active agents, including, but not limited to, pharmaceutical and therapeutic agents to animals often are severely limited by chemical and physical barriers imposed by the body. Oral delivery of many biologically-active agents would be the route of choice if not for the presence of chemical and physico-chemical barriers such as extreme and varying pH in the gastro-intestinal (GI) tract, exposure to powerful digestive enzymes, and impermeability of gastro-intestinal membranes to the active ingredient. Among the numerous pharmacological agents which are not suitable for oral administration are biologically-active peptides such as calcitonin and insulin. Examples of other compounds which are affected by the physico-chemical barriers are polysaccharides and mucopolysaccharides, including, but not limited to, heparin, heparinoids, antibiotics and other organic substrates. These agents are rapidly destroyed in the gastro-intestinal tract by acid hydrolysis, enzymes, or the like.

Prior methods for orally administering vulnerable pharmacological agents have relied on co-administration of adjuvants (e.g., resorcinols and non-ionic surfactants such as polyoxyethylene oleyl ether and n-hexadecyl polyethylene ether) to increase artificially the permeability of the intestinal walls; and on co-administration of enzymatic inhibitors (e.g., pancreatic trypsin inhibitor, diisopropylfluorophosphate (DFF) and trasylol) to avoid enzymatic degradation. Liposomes have also been described as drug delivery systems for insulin and heparin. See, for instance, U.S. Pat. No. 4,239,754; Patel et al. (1976) *FEBS Letters* Vol. 62, page 60; and Hashimoto et al. (1979) *Endocrinol. Japan*, Vol. 26, page 337. The broader use of the aforementioned methods, however, as drug delivery systems are precluded for reasons which include: (1) the use of toxic amounts of adjuvants or inhibitors; (2) the lack of suitable low MW cargoes; (3) the poor stability and inadequate shelf life of the systems; (4) difficulty in manufacturing; and (5) the failure of the systems to protect the active ingredient; and (6) the failure of the systems to promote absorption of the active agent.

More recently, microspheres of artificial polymers, or proteinoids, of mixed amino acids have been described for delivery of pharmaceuticals. For example, U.S. Pat. No. 4,925,673 describes such microspheres as well as methods for their preparation and use. The proteinoid microspheres of the '673 patent are useful for encapsulating a number of active agents.

There is a need in the art for a simple and inexpensive delivery system which is easily prepared and which can deliver a broad range of biologically-active agents.

SUMMARY OF THE INVENTION

Compositions for delivering biologically-active agents incorporating modified amino acids as carriers are provided.

The compositions comprise;

(A) at least one biologically active agent, and (B)
  (a) at least one acylated amino acid;
  (b) at least one peptide comprising at least one acylated amino acid; or
  (c) a combination of (a) and (b);

wherein said acylated amino acid is acylated by (i) a $C_3$–$C_{10}$ cycloalkyl acylating agent, said agent optionally being substituted with $C_1$–$C_7$ alkyl, $C_2$–$C_7$ alkenyl, $C_1$–$C_7$ alkoxy, hydroxy, phenyl, phenoxy, or —$CO_2R$, wherein R is hydrogen, $C_1$–$C_4$ alkyl or $C_2$–$C_4$ alkenyl; or (ii) a $C_3$–$C_{10}$ cycloalkyl substituted $C_1$–$C_6$ alkyl acylating agent.

In an alternative embodiment, these compositions are used in oral dosage unit forms. The compositions or oral dosage unit forms can be orally administered to animals.

DETAILED DESCRIPTION OF THE INVENTION

Figure 1:
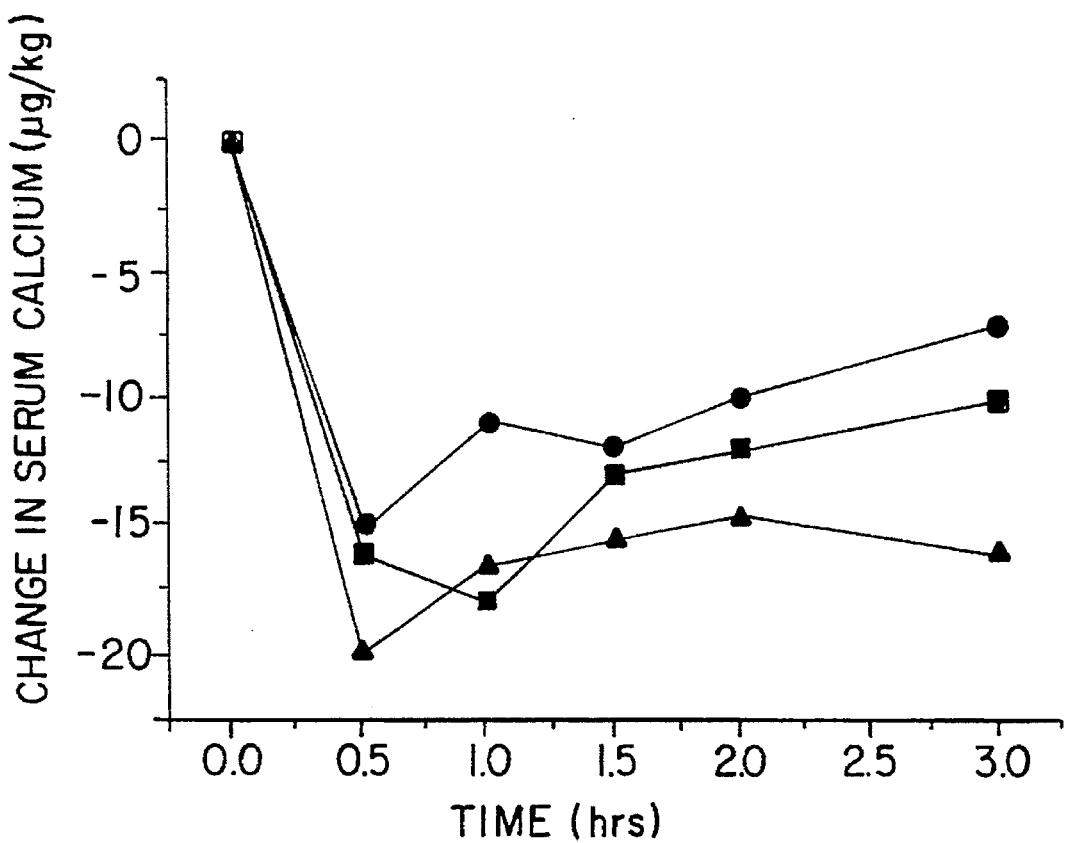
FIG. 1 is a graphic illustration of the results of oral gavage testing in rats using calcitonin with cyclohexanoyl-(L)-leucine, cycloheptanoyl-(L)-leucine and 2-methylcyclohexanoyl-(L)-leucine carriers.

Modified amino acids and peptides that include at least one modified amino acid may be used as carriers to deliver biologically-active agents such as peptides, mucopolysaccharides, carbohydrates, lipids, and pesticides. These carriers particularly are useful in facilitating the delivery of orally sensitive biologically active agents. For example, hormones such as calcitonin, insulin and polysaccharides such as heparin, are not considered orally administrable for various reasons. Insulin, for example, is sensitive to the denaturing conditions of the gastrointestinal (GI) tract. Also, heparin, by virtue of its charge and hydrophilic nature, is not readily absorbed from the gut. In contrast to the modified amino acids and peptides of the present invention, unmodified free amino acids provide inadequate protection against degradation in the GI tract for labile bioactive agents.

The compositions of the subject invention are useful for administering biologically-active agents to any animals such as birds; mammals, such as primates and particularly humans; and insects.

The present invention, in several embodiments, uses readily available and inexpensive starting materials, and provides a cost-effective method for preparing and isolating modified amino acids and peptides. The method is simple to perform and is amenable to industrial scale-up for commercial production.

Biologically-active agents suitable for use with carriers disclosed herein include, but are not limited to, peptides, and particularly small peptide hormones, which by themselves pass slowly or not at all through the gastro-intestinal mucosa and/or are susceptible to chemical cleavage by acids and enzymes in the gastrointestinal tract; polysaccharides and particularly mixtures of mucopolysaccharides, carbohydrates; lipids; or any combination thereof. Examples include, but are not limited to, human growth hormone; bovine growth hormone; growth hormone releasing hormone; interferons; interleukin-I; insulin; heparin, and particularly low molecular weight heparin; calcitonin; erythropoietin; atrial naturetic factor; antigens; monoclonal antibodies; somatostatin; adrenocorticotropin; gonadotropin releasing hormone; oxytocin; vasopressin; vancomycin; cromylyn sodium; desferrioxamine (DFO); or any combination thereof.

Additionally the carriers of the present invention can be used to deliver other active agents such as pesticides and the like.

An amino acid is any carboxylic acid having at least one free amine group and includes naturally occurring and synthetic amino acids. The preferred amino acids for use in the present invention are ∝-amino acids, and most preferably are naturally occurring ∝-amino acids. Poly amino acids are either peptides or two or more amino acids linked by a bond formed by other groups which can be linked, e.g., an ester, anhydride or an anhydride linkage. Special mention is made of non-naturally occurring poly amino acids and particularly non-naturally occurring hetero poly amino acids, i.e. of mixed amino acids.

Peptides are two or more amino acids joined by a peptide bond. Peptides can vary in length from di-peptides with two amino acids to polypeptides with several hundred amino acids. See, Walker, *Chambers Biological Dictionary*, Cambridge, England: Chambers Cambridge, 1989, page 215. Special mention is made of non-naturally occurring peptides and particularly non-naturally occurring peptides of mixed amino acids. The peptides most useful in the practice of the present invention include di-peptides, tri-peptides, tetra-peptides, and penta-peptides. The preferred peptides are di-peptides, and tri-peptides. Peptides can be homo- or hetero- peptides and can include natural amino acids, synthetic amino acids, or any combination thereof.

Amino acids suitable fur use in the present invention are generally of the formula

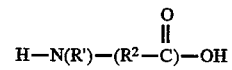

wherein:

$R^1$ is hydrogen, $C_1$–$C_4$ alkyl, or $C_2$–$C_4$ alkenyl;

$R^2$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkenyl);

$R^2$ being optionally substituted with $C_1$–$C_4$ alkyl, $C_2$–$C_4$ alkenyl, $C_1$–$C_4$ alkoxy, —OH, —SH, —$CO_2R^3$, $C_3$–$C_{10}$ cycloalkyl, $C_3$–$C_{10}$ cycloalkenyl, heterocycle having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^2$ being optionally interrupted by oxygen, nitrogen, sulfur, or any combination thereof; and $R^3$ is hydrogen, $C_1$–$C_4$ alkyl, or $C_2$–$C_4$ alkenyl.

The preferred naturally occurring amino acids for use in the present invention as amino acids or components of a peptide are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine. The preferred amino acids are arginine, leucine, lysine, phenylalanine, tyrosine, tryptophan, valine, and phenylglycine.

The preferred non-naturally occurring amino acids for use in the present invention are β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, 1,2,3,4,-tetrahydroisoquinoline-3-carboxylic acid and thioproline.

The amino acids or peptides are modified by acylating at least one free amine group, with an acylating agent which reacts with at least one of the free amine groups present. Suitable, but non-limiting, examples of acylating agents useful for modifying amino acids or peptide derivatives useful in practicing the present invention include acylating agents, and particularly acid chloride acylating agents, having the formula

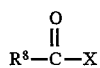

wherein

R⁸ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy, or —$CO_2R^9$ wherein $R^9$ is hydrogen, $C_1$–$C_4$ alkyl or $C_2$–$C_4$ alkenyl; or (ii) $C_3$–$C_{10}$ cycloalkyl substituted $C_1$–$C_6$ alkyl; and X is a leaving group. Preferably, $R^8$ is cyclopropyl, cyclopentyl, cyclohexyl or cycloheptyl.

In a reaction in which the substrate molecule becomes cleaved, part of it (the part not containing the carbon) is usually called the leaving group. See *Advanced Organic Chemistry*, 2d edition, Jerry March, New York: McGraw-Hill Book (1977). Typical leaving groups include, but are not limited to, halogens such as chlorine, bromine and iodine.

Preferred acylating agents include, but are not limited to, acyl halides such as cyclohexanoyl chloride, cyclopentanoyl chloride, cycloheptanoyl chloride and the like; and anhydrides, such as cyclohexanoic anhydride, cyclopentanoic anhydride, cycloheptanoic anhydride, cycloheptanoic anhydride, and the like. Most preferred acylating agents are cyclohexanoyl chloride, cyclopentanoyl chloride, and cycloheptanoyl chloride.

Preferred acylated amino acids of the present invention have the formula

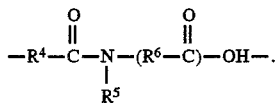

wherein:

$R^4$ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy or —$CO_2R^7$, wherein $R^7$ is hydrogen, $C_1$–$C_4$ alkyl, or $C_2$–$C_4$ alkenyl; or (ii) $C_1$–$C_6$ alkyl substituted with $C_3$–$C_{10}$ cycloalkyl;

$R^5$ is hydrogen, $C_1$–$C_4$ alkyl, or $C_2$–$C_4$ alkenyl;

$R^6$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkenyl) phenyl, ($C_2$–$C_{10}$ alkyl), phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl, naphtyl, ($C_1$–$C_{10}$ alkyl) or naphthyl ($C_2$–$C_{10}$ alkenyl);

$R^6$ being optionally substituted with $C_1$–$C_4$ alkyl, $C_2$–$C_4$ alkenyl, $C_1$–$C_4$ alkoxy, —OH, —SH, —$CO_2R^7$, $C_3$–$C_{10}$ cycloalkyl, $C_3$–$C_{10}$ cycloalkenyl, heterocycle having 3–10 ring atoms wherein the hetero atom is one or more of N, O, S or any combination thereof, aryl, ($C_1$–$C_{10}$ alk)aryl, ar($C_1$–$C_{10}$ alkyl), or any combination thereof;

$R^6$ being optionally interrupted by oxygen, nitrogen, sulfur, or any combination thereof; and $R^7$ is hydrogen, $C_1$–$C_4$ alkyl, or $C_2$–$C_4$ alkenyl.

The modified amino acids of the present invention may be prepared by reacting single amino acids, mixtures of two or more amino acids, amino acid esters, or amino acid amides, with an amine modifying agent which reacts with free amino moieties present in the amino acids to form amides. Amino acids and amino acid esters are readily available from a number of commercial sources such as Aldrich Chemical Co. (Milwaukee, Wis., U.S.A.); Sigma Chemical Co. (St. Louis, Mo., U.S.A.); and Fluka Chemical Corp. (Ronkonkoma, N.Y., U.S.A.).

The modified amino acids can be readily prepared by methods known to those skilled in the art. For example, the amino acids are dissolved in an aqueous alkaline solution of a metal hydroxide, e.g., sodium or potassium hydroxide and the acylating agent added. The reaction time can range from about 1 hour and about 4 hours, preferably about 2–2.5 hours. The temperature of the mixture is maintained at a temperature generally ranging between about 5° C. and about 70° C., preferably between about 10° C. and about 50° C. The amount of alkali employed per equivalent of $NH_2$ groups in the amino acids generally ranges between about 1.25 moles and about 3 moles, and is preferably between about 1.5 moles and about 2.25 moles per equivalent of $NH_2$. The pH of the reaction solution generally ranges between about pH 8 and about pH 13, and is preferably between about pH 10 and about pH 12. The amount of amino modifying agent employed in relation to the quantity of amino acids is based on the moles of total free $NH_2$ in the amino acids. In general, the amino modifying agent is employed in an amount ranging between about 0.5 and about 2.5 mole equivalents, preferably between about 0.75 and about 1.25 equivalents, per molar equivalent of total $NH_2$ groups in the amino acids.

The modified amino acid formation reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded and modified amino acids are collected by filtration or decantation. The crude modified amino acids are then mixed with water. Insoluble materials are removed by filtration and the filtrate is dried in vacuo. The yield of modified amino acids generally ranges between about 30 and about 60%, and usually about 45%. The present invention also contemplates amino acids which have been modified by multiple acylation, e.g., diacylation or triacylation.

If desired, esters or amides of amino acids may be used to prepare the modified amino acids of the invention. The amino acid esters or amides, dissolved in a suitable organic solvent such as dimethylformamide or pyridine, are reacted with the amino modifying agent at a temperature ranging between about 5° C. and about 70° C., preferably about 25° C., for a period ranging between about 7 and about 24 hours. The amount of amino modifying agents used relative to the amino acid esters are the same as described above for amino acids.

Thereafter, the reaction solvent is removed under negative pressure and optionally the ester or amide functionality can be removed by hydrolyzing the modified amino acid ester with a suitable alkaline solution, e.g., 1N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g., with an aqueous 25% hydrochloric acid solution, to a pH ranging between about 2 and about 2.5. The modified amino acid precipitates out of solution and is recovered by conventional means such as filtration or decantation.

The modified amino acids may be purified by acid precipitation, recrystallization or by fractionation on solid column supports. Fractionation may be performed on a suitable solid column supports such as silica gel, alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The modified amino acids may also be purified by extraction with a lower alcohol such as methanol, butanol, or isopropanol to remove impurities such as inorganic salts.

The modified amino acids of the present invention generally are soluble in alkaline aqueous solution (pH≧9.0); partially soluble in ethanol, n-butanol and 1:1 (v/v) toluene/ethanol solution and insoluble in neutral water. The alkali metal salts, e.g., the sodium salt of the deritivatized amino acids are generally soluble in water at about a pH of 6–8.

Modified peptides may include one or more acylated amino acid. Although linear modified peptides will generally include only one acylated amino acid, other peptide configurations such as, but not limited to, branched peptides can include more than one acylated amino acid. Peptides can be polymerized with the acylated amino acid(s) or can be acylated after polymerization. Special mention is made of compounds having the formula:

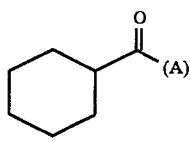

wherein

A is Try, Leu, Arg, Trp, or Cit; and optionally wherein if A is Try, Arg, Trp or Cit; A is acylated at 2 or more functional groups.

Preferred compounds are those wherein A is Try; A is Tyr and is acylated at 2 functional groups; A is Leu; A is Arg; A is Arg and is acylated at 2 functional groups; A is Trp; A is Trp and is acylated at 2 functional groups; A is Cit; and A is Cit and is acylated at 2 functional groups.

Special mention is also made of compounds having the formula:

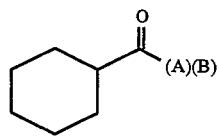

wherein A is Arg or Leu and B is Arg or Leu

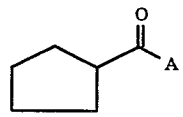

wherein A is Arg or Leu; and wherein if A is Arg, A is optionally acylated at 2 or more functional groups;

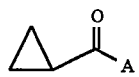

where A is Leu or phenylglycine;

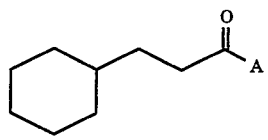

wherein A is phenylglycine; and

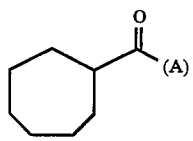

wherein A is phenylglycine.

If the amino acid is multifunctional, i.e. has more than one —OH, —NH$_2$ or —SH group, then it may optionally be acylated at one or more functional groups to form, for example, an ester, amide, or thioester linkage.

In one embodiment, the modified amino acids or peptides may be used directly as a drug delivery carrier by simply mixing one or more modified amino acids or peptides with the active ingredient prior to administration. In an alternative embodiment, the modified amino acids may be used to form microspheres containing the active agent. The modified amino acids or peptides of the invention are particularly useful for the oral administration of certain biologically-active agents, e.g., small peptide hormones, which, by themselves, do not pass or only pass slowly through the gastro-intestinal mucosa and/or are susceptible to chemical cleavage by acids and enzymes in the gastrointestinal tract.

If the modified amino acids or peptides are to be converted into microspheres such as proteinoid microspheres, the mixture is optionally heated to a temperature ranging between about 20° and about 50° C., preferably about 40° C., until the modified amino acid(s) dissolve. The final solution contains between from about 1 mg and to about 2000 mg of modified amino acids or peptides per mL of solution, preferably between about 1 and about 500 mg per mL. The concentration of active agent in the final solution varies and is dependent on the required dosage for treatment. When necessary, the exact concentration can be determined by, for example, reverse phase HPLC analysis.

When the modified amino acids or peptides are used to prepare microspheres, another useful procedure is as follows: Modified amino acids or peptides are dissolved in deionized water at a concentration ranging between about 75 and about 200 mg/ml, preferably about 100 mg/ml at a temperature between about 25° C. and about 60° C., preferably about 40° C. Particulate matter remaining in the solution may be removed by conventional means such as filtration.

Thereafter, the modified amino acid or peptide solution, maintained at a temperature of about 40° C., is mixed 1:1 (V/V) with an aqueous acid solution (also at about 40° C.) having an acid concentration ranging between about 0.05N and about 2N, preferably about 1.7N. The resulting mixture is further incubated at 40° C. for a period of time effective for microsphere formation, as observed by light microscopy. In practicing this invention, the preferred order of addition is to add the modified amino acid or peptide solution to the aqueous acid solution.

Suitable acids for microsphere formation include any acid which does not (a) adversely effect the modified amino acids, or peptides e.g., initiate or propagate chemical decomposition;

(b) interfere with microsphere formation;
(c) interfere with microsphere incorporation of the cargo; and
(d) adversely interact with the cargo.

Preferred acids for use in this invention include acetic acid, citric acid, hydrochloric acid, phosphoric acid, malic acid and maleic acid.

In practicing the invention, a microsphere stabilizing additive may be incorporated into the aqueous acid solution or into the modified amino acid or protein solution prior to the microsphere formation process. With some drugs the presence of such additives promotes the stability and/or dispersibility of the microspheres in solution.

The stabilizing additives may be employed at a concentration ranging between about 0.1 and 5% (w/v), preferably about 0.5% (w/v). Suitable, but non-limiting, examples of microsphere stabilizing additives include gum acacia, gelatin, methyl cellulose, polyethylene glycol, and polylysine. The preferred stabilizing additives are gum acacia, gelatin and methyl cellulose.

Under the above conditions, the modified amino acid molecules or peptides form hollow or solid matrix type microspheres wherein the cargo is distributed in a carrier matrix or capsule type microspheres encapsulating liquid or solid cargo. If the modified amino acid or peptide microspheres are formed in the presence of a soluble material, e.g., a pharmaceutical agent in the aforementioned aqueous acid solution, this material will be encapsulated within the microspheres. In this way, one can encapsulate pharmacologically active materials such as peptides, proteins, and polysaccharides as well as charged organic molecules, e.g., antimicrobial agents, which normally have poor bioavailability by the oral route. The amount of pharmaceutical agent which may be incorporated by the microsphere is dependent on a number of factors which include the concentration of agent in the solution, as well as the affinity of the cargo for the carrier. The modified amino acid or peptide microspheres of the invention do not alter the physiological and biological properties of the active agent. Furthermore, the encapsulation process does not alter the pharmacological properties of the active agent. Any pharmacological agent can be incorporated within the amino acid microspheres. The system is particularly advantageous for delivering chemical or biological agents which otherwise would be destroyed or rendered less effective by conditions encountered within the body of the animal to which it is administered, before the microsphere reaches its target zone (i.e., the area in which the contents of the microsphere are to be released) and pharmacological agents which are poorly absorbed in the gastro-intestinal tract. The target zones can vary depending upon the drug employed.

The particle size of the microsphere plays an important role in determining release of the active agent in the targeted area of the gastro-intestinal tract. The preferred microspheres have diameters between about ≦0.1 microns and about 10 microns, preferably between about 0.5 microns and about 5 microns. The microspheres are sufficiently small to release effectively the active agent at the targeted area within the gastro-intestinal tract such as, for example, between the stomach and the jejunum. Small microspheres can also be administered parenterally by being suspended in an appropriate carrier fluid (e.g., isotonic saline) and injected directly into the circulatory system, intramuscularly or subcutaneously. The mode of administration selected will vary, of course, depending upon the requirement of the active agent being administered. Large amino acid microspheres (>50 microns) tend to be less effective as oral delivery systems.

The size of the microspheres formed by contacting modified amino acids or peptides with water or an aqueous solution containing active agents can be controlled by manipulating a variety of physical or chemical parameters, such as the pH, osmolarity or ionic strength of the encapsulating solution, size of the ions in solution and by the choice of acid used in the encapsulating process.

Typically, the pharmacological compositions of the present invention are prepared by mixing an aqueous solution of the carrier with an aqueous solution of the active ingredient, just prior to administration. Alternatively, the carrier and biologically active ingredient can be admixed during the manufacturing process. The solutions may optionally contain additives such as phosphate buffer salts, citric acid, acetic acid, gelatin and gum acacia.

In practicing the invention, stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, and polylysine. The preferred stabilizing additives are gum acacia, gelatin and methyl cellulose.

The amount of active agent in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of carrier/biologically-active agent compositions or may contain a divided pharmacologically or biologically effective amount. The total effective amounts will be administered by cumulative units containing, in total, pharmacologically or biologically active amounts of biologically-active agent.

The total amount of biologically-active agent to be used can be determined by those skilled in the art. However, it has surprisingly been found that with certain biologically-active agents, such as calcitonin, the use of the presently disclosed carriers provides extremely efficient delivery. Therefore, lower amounts of biologically-active agent than those used in prior dosage unit forms or delivery systems can be administered to the subject, while still achieving the same blood levels and therapeutic effects.

The amount of carrier in the present composition is a delivery effective amount and can be determined for any particular carrier or biologically-active agent by methods known to those skilled in the art.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

Administration of the present compositions or dosage unit forms preferably is oral or by intraduodenal injection.

EXAMPLES

The invention will now be illustrated in the following non-limiting examples which are illustrative of the invention but are not intended to limit the scope of the invention.

Example 1

PREPARATION OF N-CYCLOHEXANOYL-(L)-TYROSINE.

(L)-Tyrosine (61.6 g., 0.34 mole) was dissolved in 190 mL of 2N sodium hydroxide. Cyclohexanoyl chloride (49.32 mL, 0.34 mole) was added dropwise to the mixture. Additional aqueous 2N sodium hydroxide was added and the reaction mixture was allowed to stir at room temperature for 2 hours. The mixture was then acidified to pH 9.5 with aqueous (4:1) hydrochloric acid. A precipitate formed which was separated by vacuum filtration. The solids were dissolved in 2N sodium hydroxide and dried by lyophilization to furnish 33.5 g of N,O-dicyclohexanoyl-(L)-tyrosine. The product was purified by column chromatography on silica gel using butanol/acetic acid/water as the eluent system. The pure product was a white solid.

1. Mass Spectrum: M+23 m/e 314.
2. $^1$H NMR (300 MHz,DMSO-d6): d=6.8 (d, 2H); 6.4 (d,2H); 4.4 (m, 1H); 2.5 (ddd,2H); 2.0 (m,2H); 1.6 (m,10H); 1.2(m, 10H).
3. IR (KBr) cm−1: 3350, 2900, 2850, 1600, 1520, 1450, 1400, 1300.

Example 2

PREPARATION OF N-CYCLOHEXANOYL-(L)-ARGININE.

(L)-Arginine (103.2 g., 0.6 mole) was dissolved in 600 mL of 2N sodium hydroxide. Cyclohexanoyl chloride (87 mL, 0.6 mole) was added dropwise to the mixture. The reaction mixture was maintained at 50° C. for 2 hours. The mixture was then cooled to room temperature and acidified to pH 2.3 with aqueous (4:1) hydrochloric acid. The precipitate which formed was separated by decantation. The solids were dissolved in 2N sodium hydroxide and dried by lyophilization to furnish 64.1 g of crude N-cyclohexanoyl-(L)-arginine. The product was purified by column chromatography on silica gel/using butanol/acetic acid/water as the eluent system. The products isolated were N-cyclohexanoyl-(L)-arginine and N(α)-N(y)-dicyclohexanoyl-(L)-arginine.

N-cyclohexanoyl-(L)-arginine:
1. Mass Spectrum: M+1 m/e 395.
2. $^1$H NMR (300 MHz, DMSO-d6): ppm δ=8.75(br, 1H); 7.6 (br, 5H); 4.0 (m, 1H); 3.05 (m, 2H); 2.15 (m, 1H); 1.1–1.5 (br.m, 14H).

N (α), N (y)-dicyclohexanoyl-(L)-arginine:
1. Mass Spectrum: M+1 m/e 285.
2. $^1$H NMR: (300 MHz, DMSO-d6): d=2.0 (m, 3H); 1.8–1.4 (br. m, 17H); 1.3–1.0 (br. m, 20H)

EXAMPLE 3

PREPARATION OF N-CYCLOHEXANOYL-(L)-CITRULLINE.

L-Citrulline (35.2 g., 0.2 mole) was dissolved in 200 mL of 2N sodium hydroxide. Cyclohexanoyl chloride (29 mL, 0.2 mole) was added dropwise to the mixture. The reaction mixture was maintained at about 25° C. for 1 hour. The mixture was then acidified to pH 2.6 with aqueous (4:1) hydrochloric acid. The precipitate which formed was separated by decantation. The solids were dissolved in 2N sodium hydroxide to pH 6.5 and dried by lyophilization to furnish 44.2 g of N-cyclohexanoyl-(L)-citrulline. The product was a white solid.

1. Mass Spectrum: M+23 m/e 308.
2. $^1$H NMR (300 MHz,DMSO-d6): d=4.1 (dd, 1H); 2.9 (t, 2H); 2.1 (m,2H); 1.6–1.2 (br.m, 14H).
3. IR (KBr) cm−1: 3400, 3300, 2950, 2850, 1700, 1650, 1600, 1450, 1400 cm−1.

EXAMPLE 4

PREPARATION OF N-CYCLOPENTANOYL-(L)-ARGININE.

(L)-Arginine (32.8 g., 0.19 moles) was dissolved in 188 mL of 2N sodium hydroxide. Cyclopentanoyl chloride (22.9 mL, 0.19 moles) were added dropwise to the mixture. The reaction mixture was maintained at about 25° C. for 2 hours. The mixture was then acidified to pH 1.5 with aqueous (4:1) hydrochloric acid. The precipitate which formed was separated by decantation. The solids were dissolved in 2N sodium hydroxide to pH 7.5 and dried by lyophilization to furnish 67.4 g of N-cyclopentanoyl-(L)-arginine. The product was a white solid. Mass Spectrum: M+1 m/e 271.

EXAMPLE 5

PREPARATION OF N-CYCLOHEXANOYL-(t)-ARGININE.

(t)-Arginine (14.2 g., 0.1 mole) was dissolved in 100 mL of 2N sodium hydroxide. Cyclohexanoyl chloride (13 mL, 0.098 mole) was added dropwise to the mixture. The reaction mixture was maintained at 25° C. for 2 hours. The mixture was then cooled to room temperature and acidified to pH 6.6 with aqueous (4:1) hydrochloric acid. The white precipitate which formed was separated by decantation. The solids were dissolved in a minimum of 2N sodium hydroxide. The product, a white solid, (11.6 g, 49%) was isolated by lowering the pH of the purified by acidification with aqueous (4:1) hydrochloric acid to a pH of about 7–9.

1. Mass Spectrum: M+1 m/e 2423
2. $^1$H NMR (300 MHz, D$_2$O): ppm δ=4.9 (s, 1H); 2.2 (m, 1H); 1.7–1.4 (m, 5H); 1.3–1.0 (m, 5H); 0.8 (s, 9H).

IR (KBr) cm−1: 3350, 2950, 2850, 1550, 1500, 1400 cm$^{-1}$

Following the procedure of Example 1 the following amino acids and peptides have been synthesized:
cyclohexanoyl-Ala, m-(cyclohexanolyamino)benzoic acid, p-(cyclohexanoylamino)benzoic acid, 4-(cyclohexanoyl-amino)butyric acid, 6-(cyclohexanoylamino)hexanoic acid, cyclohexanoylanthranilic acid, cyclohexanoyl-Arg-Leu, cyclohexanoyl-Asp, isatoicanhydride-Asp, cyclohexanoyl-Glu, cyclohexanoyl-Gly, cyclohexanoyl-Gly-Arg, cyclohexanoyl-Ile, cyclohexanoyl-Leu, cyclopentanoyl-Leu, cyclopropanoyl-Leu, 3-methylcyclohexanoyl-Leu, 2-methylcyclohexanoyl-Leu, 4-methylcyclohexanoyl-Leu, cyclohexanoyl-(D)-Leu, cyclohexanoyl-(t)-Leu, cyclohexanoyl-Leu-Arg, cyclohexanoyl-Leu-Leu, cyclohexanoyl-(D)-Leu-(L)-Leu, cyclohexanoyl-Leu-Lys-Val, cyclohexanoyl-Lys, cyclohexanoyl-Orn, cyclohexanoyl-Phe, cycloheptanoyl-Phg, cyclohexylpropanoyl-Phg, cyclohexanoyl-Phg, cyclopentanoyl-Phg, cyclopropanoyl-Phg, 4-methylcyclohexanoyl-Phg, cyclohexanoyl-(D)-Phg, cyclohexanoyl-Tio, cyclohexanoyl-Trp, cyclohexanoyl-Tyr-Leu, cyclohexanoyl-Val, cyclopentanoyl-Val, cyclohexanoyl-Val-Val, cycloheptanoyl-Leu, and cyclohexylpropanoyl-Leu.

EXAMPLE 6

PREPARATION OF CALCITONIN DOSING SOLUTIONS:

In a test tube 400 mg of cyclohexanoyl-(L)-leucine was added to 2.9 ml of 15% ethanol. The solution was stirred and NaOH (1.0N) was added to raise the pH to 7.2. Water was added to bring the total volume to 4.0 mL. The sample had a carrier concentration of 200 mg/mL. Calcitonin (10µg) was added to the solution. The total calcitonin concentration was 2.5µg/mL.

Following a similar procedure a second solution having 400 mg of cycloheptanoyl-(L)-leucine as the carrier and a third solution having 2-methylcyclohexanoyl-(L)-leucine as the carrier were prepared. Each solution had a calcitonin concentration of 2.5µg/mL.

Example 7

CALCITONIN In Vivo EXPERIMENTS IN RATS

For each sample a group of fasted rats were anesthetized. The rats were administered, by oral gavage or by intraduodenal injection, one of the calcitonin/carrier dosages prepared in Example 6. The calcitonin concentration in each sample was 2.5µg/ml. Each rat was administered a dosage of four (4) mL/kg each. Blood samples were collected serially from the tail artery. Serum calcium was determined by testing with a Demand™ Calcium Kit (available from Sigma Chemical Company, St. Louis, Mo., U.S.A.). The results of the test are illustrated in FIG. 1.

Example 8

Figure 2:
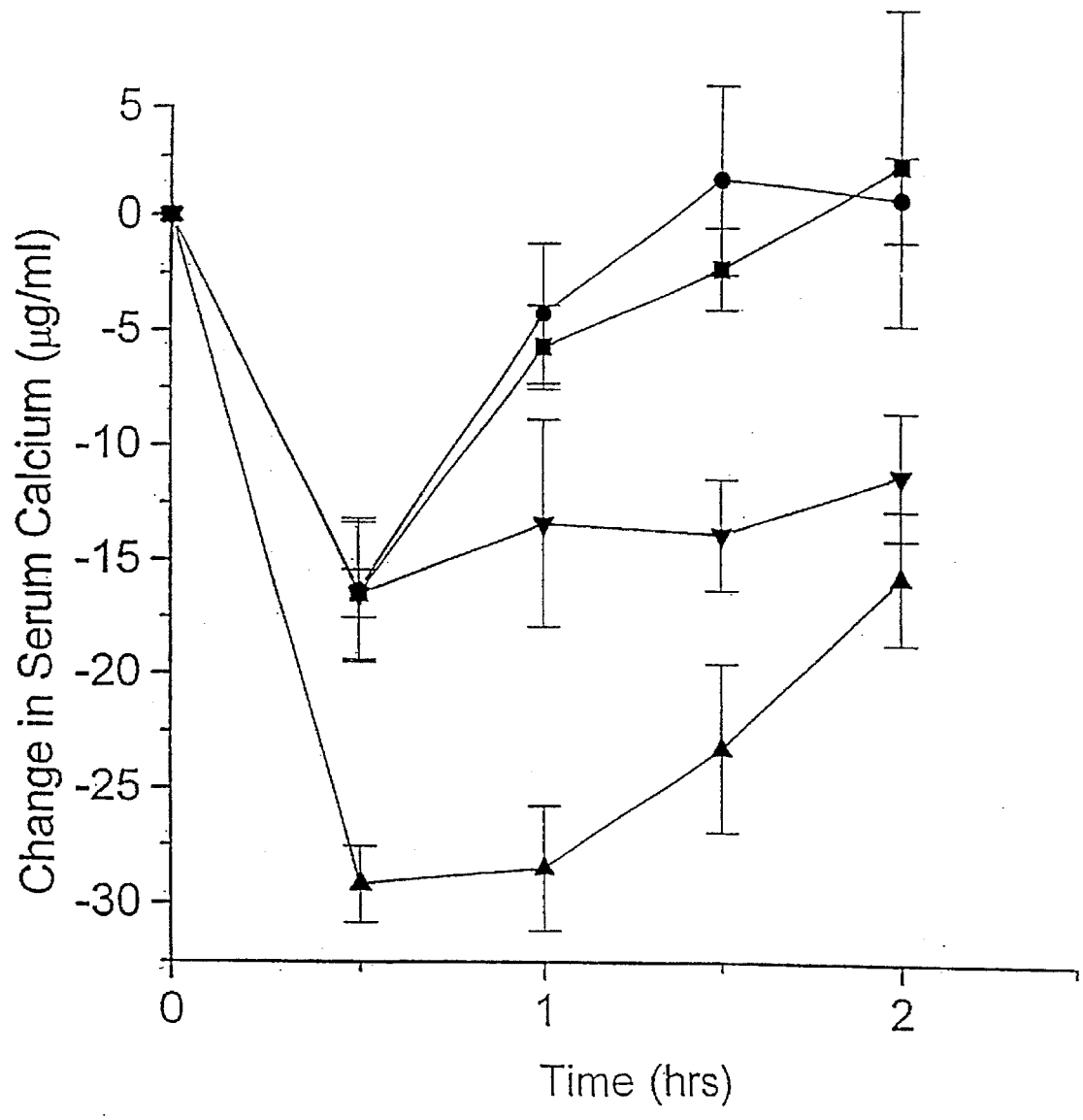
FIG. 2 is a graphic illustration of the results of oral gavage testing in rats using calcitonin with cyclohexanoyl-(L)-arginine, cyclopentanoyl-(L)-arginine, and cyclohexanoyl-(L)ophenylglycine carriers.

Three samples having 400 mg/kg of cyclohexanoyl-(L)-arginine and 10µg/kg of calcitonin, 400 mg/kg of cyclopentanoyl-(L)-arginine and 10µg/kg of calcitonin, 400 mg/kg of cyclohexanoyl-(L)-phenylglycine and 10µg/kg of calcitonin, respectively were prepared. The samples were given to fasted rats as described in Example 7. The results of the test are illustrated in FIG. 2.

Example 9

Figure 3:
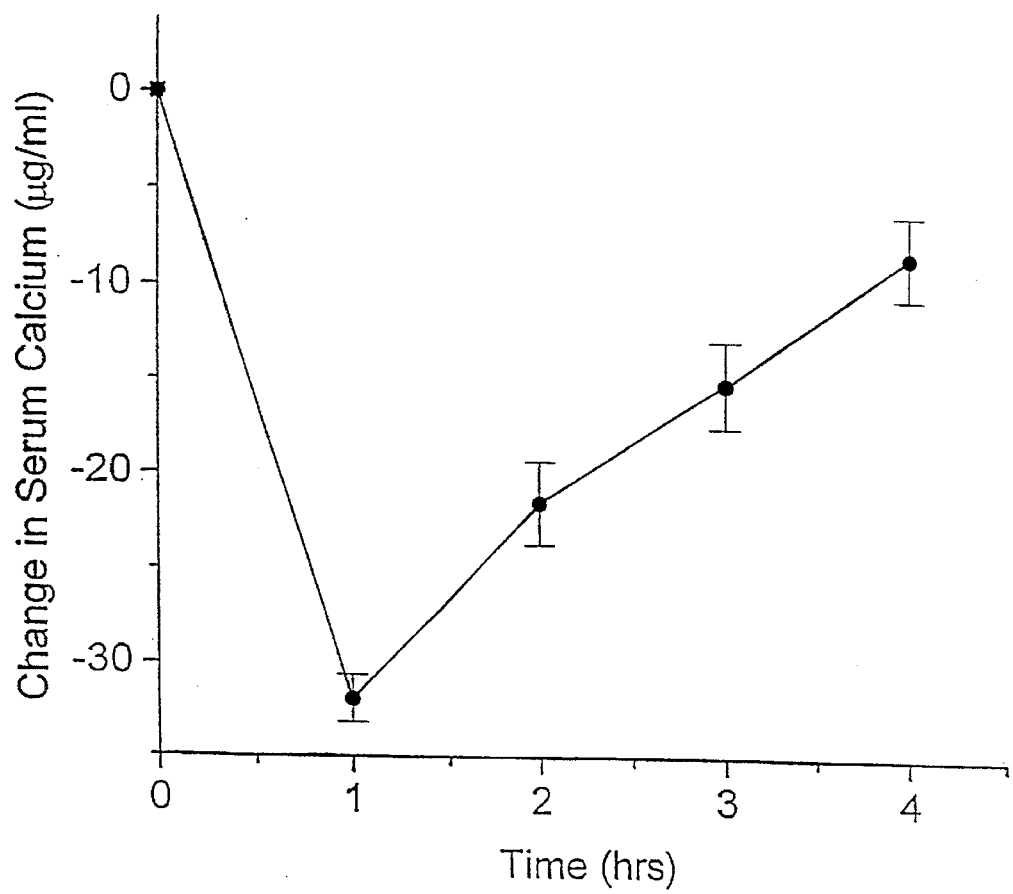
FIG. 3 is a graphic illustration of the results of oral gavage testing in rats using calcitonin with cyclohexanoyl-(L)-arginine, cyclohexanoyl-(L)-leucine, and cyclohexanoyl-(L)-tyrosine carriers.

A sample having a mixture of 266 mg/kg of cyclohexanoyl-(L)-arginine 266 mg/kg of cyclohexanoyl-(L)-leucine 266 mg/kg of cyclohexan-oyl-(L)-tyrosine and 10µg/kg of calcitonin, was prepared. The sample was given to fasted rats as described in Example 7. The results of the test are illustrated in FIG. 3.

Example 10

Figure 4:
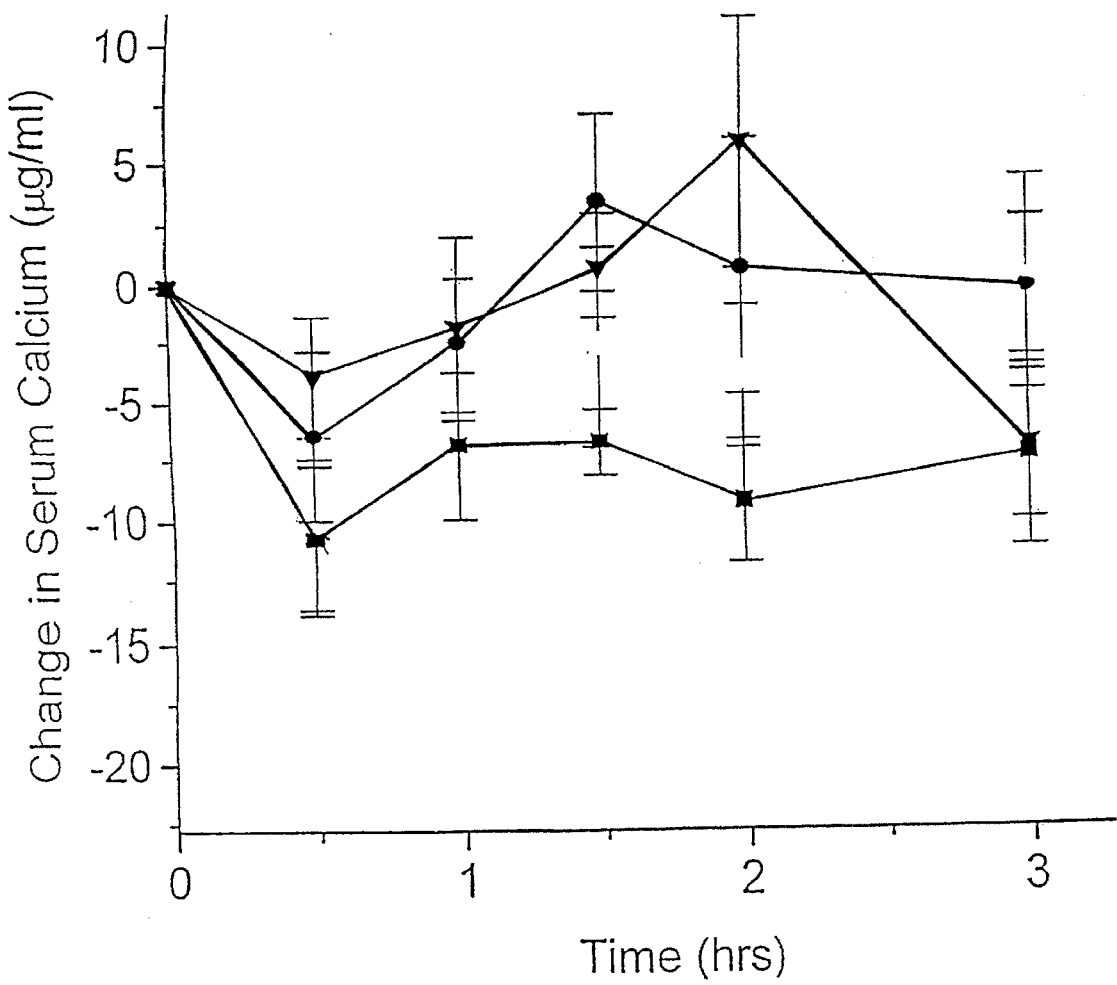
FIG. 4 is a graphic illustration of the results of oral gavage testing in rats using calcitonin with cyclohexanoyl-(L)-leucine, cyclohexanoy-(L)-glycine and cyclopropanoyl-(L)-leucine carriers.

A series of samples having 400 mg/kg of cyclohexanoyl-(L)-leucine and 3µg/kg of calcitonin, 400 mg/kg of cyclohexanoyl-(L)-glycine and 3µg/kg of calcitonin, 400 mg/kg of cyclopropanoyl-(L)-leucine and 3µg/kg of calcitonin, respectively were prepared. The samples were given to fasted rats as described in Example 7. The results of the test are illustrated in FIG. 4.

EXAMPLE 11

Figure 5:
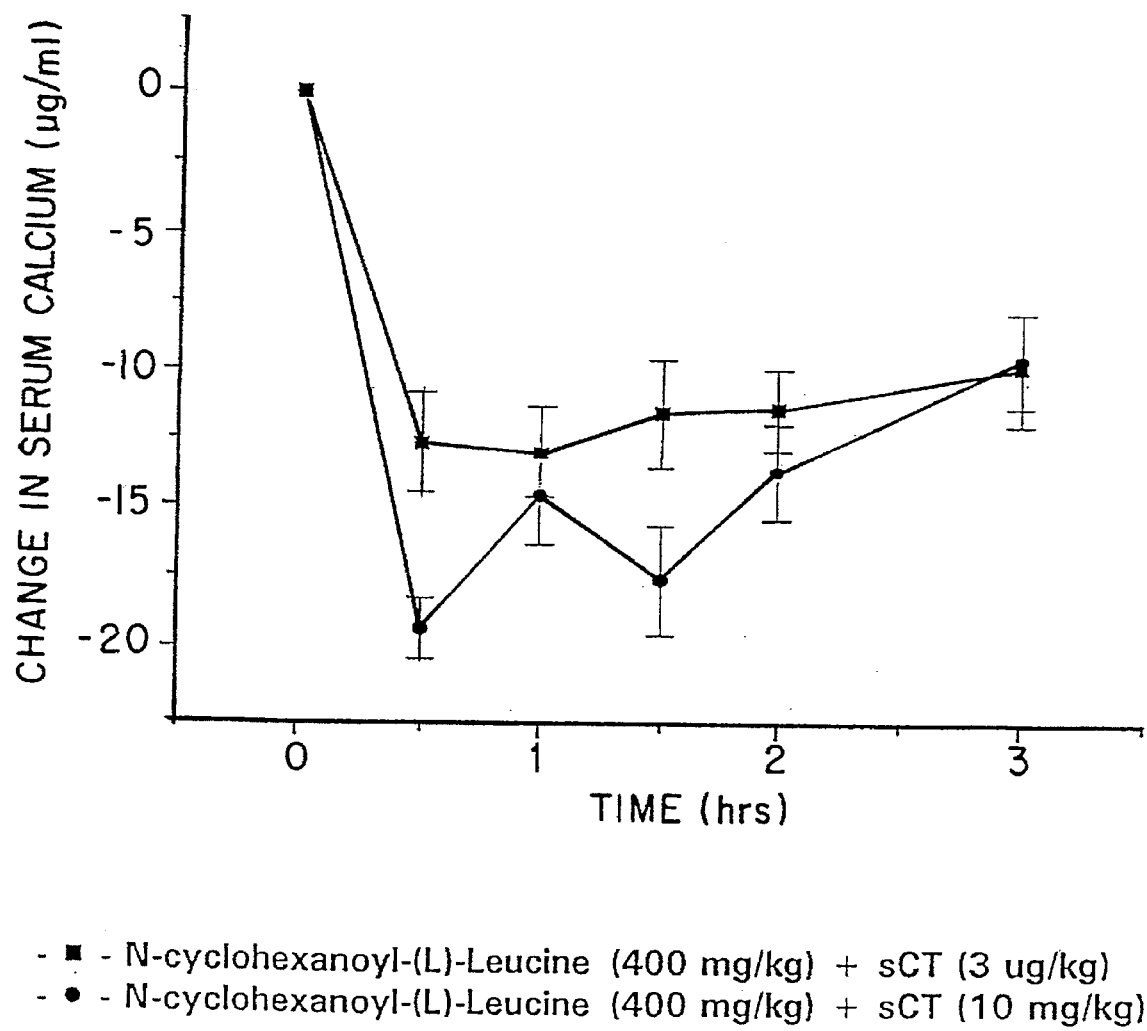
FIG. 5 is a graphic illustration of the results of oral gavage testing in rats using calcitonin with cyclohexanoyl-(L)-leucine carrier.

Two samples were prepared, having 400 mg/kg of cyclohexanoyl-(L)-leucine and 10µg/kg of calcitonin, and cyclohexanoyl-(L)-leucine and 3µg/kg of calcitonin, respectively. The samples were given to fasted rats as described in Example 7. The results of the test are illustrated in FIG. 5.

EXAMPLE 12

PREPARATION OF HEPARIN DOSING SOLUTIONS:

Following the general procedure published by Santiago, N. in *Proc. Int. Symp. Control Rel. Bioact. Mat.,* Vol. 19. pages 514–515, (1992)the heparin samples were prepared. In a test tube 900 mg of cyclohexanoyl-(L)-leucine was added to 4.5. mL of water. Heparin (74.7 mg) was dissolved in 4.5 mL of a solution of 1.7N citric acid and 0.5% gum arabic. The solutions were warmed to about 40° C. and mixed. The sample had a carrier concentration of 100 mg/mL. The heparin concentration was 8.3 mg/mL.

Following a similar procedure a second sample having 900 mg of cyclohexanoyl-(L)-leucine and heparin (150 mg) was prepared. The heparin concentration was 16.7 mg/mL.

EXAMPLE 13

HEPARIN In Vivo EXPERIMENTS IN RATS

Figure 6:
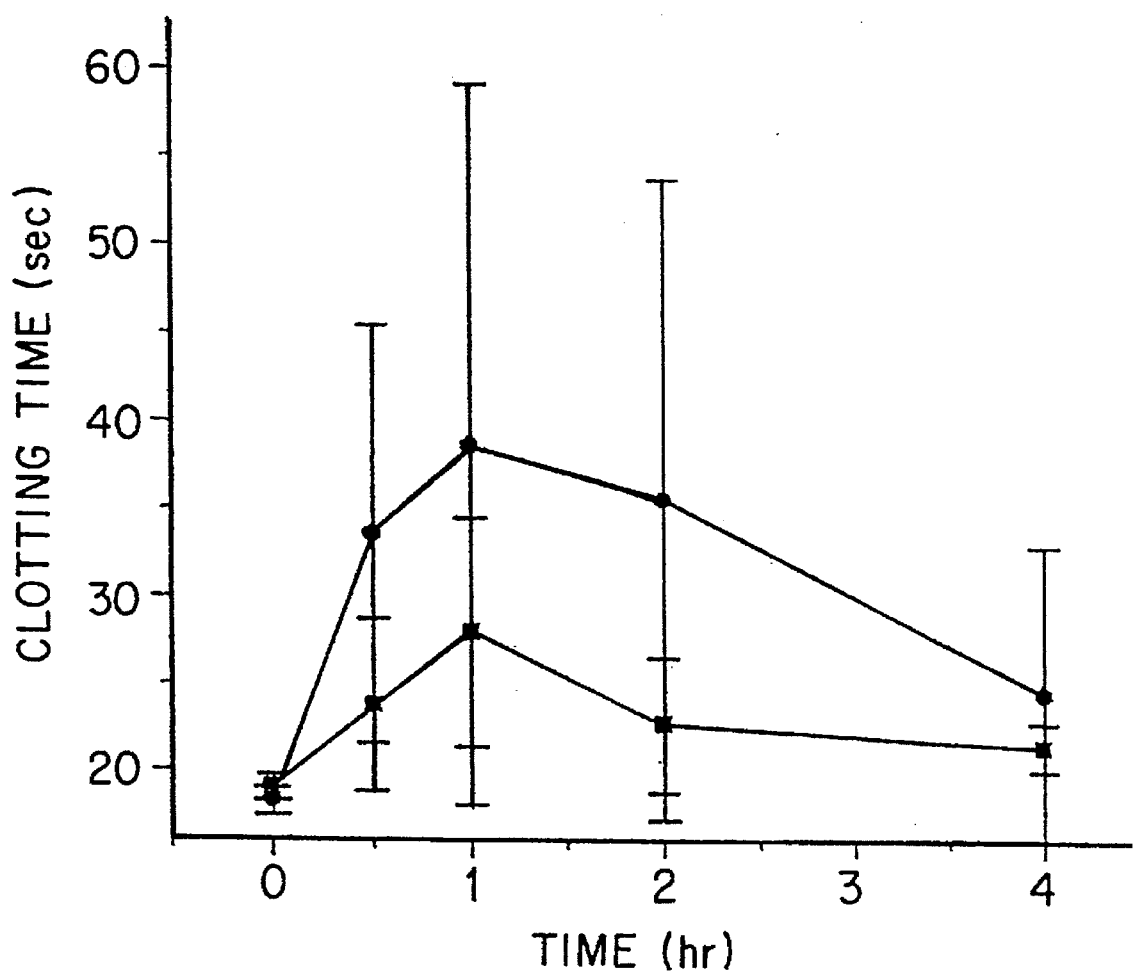
FIGS. 6 and 7 are graphic illustrations of the results of oral gavage testing in rats using heparin with cyclohexanoyl-(L)-leucine carrier.

For each sample a group of fasted rats were anesthetized. The rats were administered, by oral gavage, one of the heparin/carrier dosages prepared in Example 11. The heparin concentration in the samples were 8.3 and 16.7 mg/ml respectively. Each rat was administered a dosage of about three (3) mL/kg each. Blood samples were collected serially from the tail artery. Heparin activity was determined by utilizing the activated partial thromboplastin time (APTT) according to the method of Henry, J. B., *Clinical Diagnosis and Management by Laboratory Methods;* Philadelphia, Pa.; W. B. Saunders (1979). The results of the test are illustrated in FIG. 6.

Example 14

Figure 7:
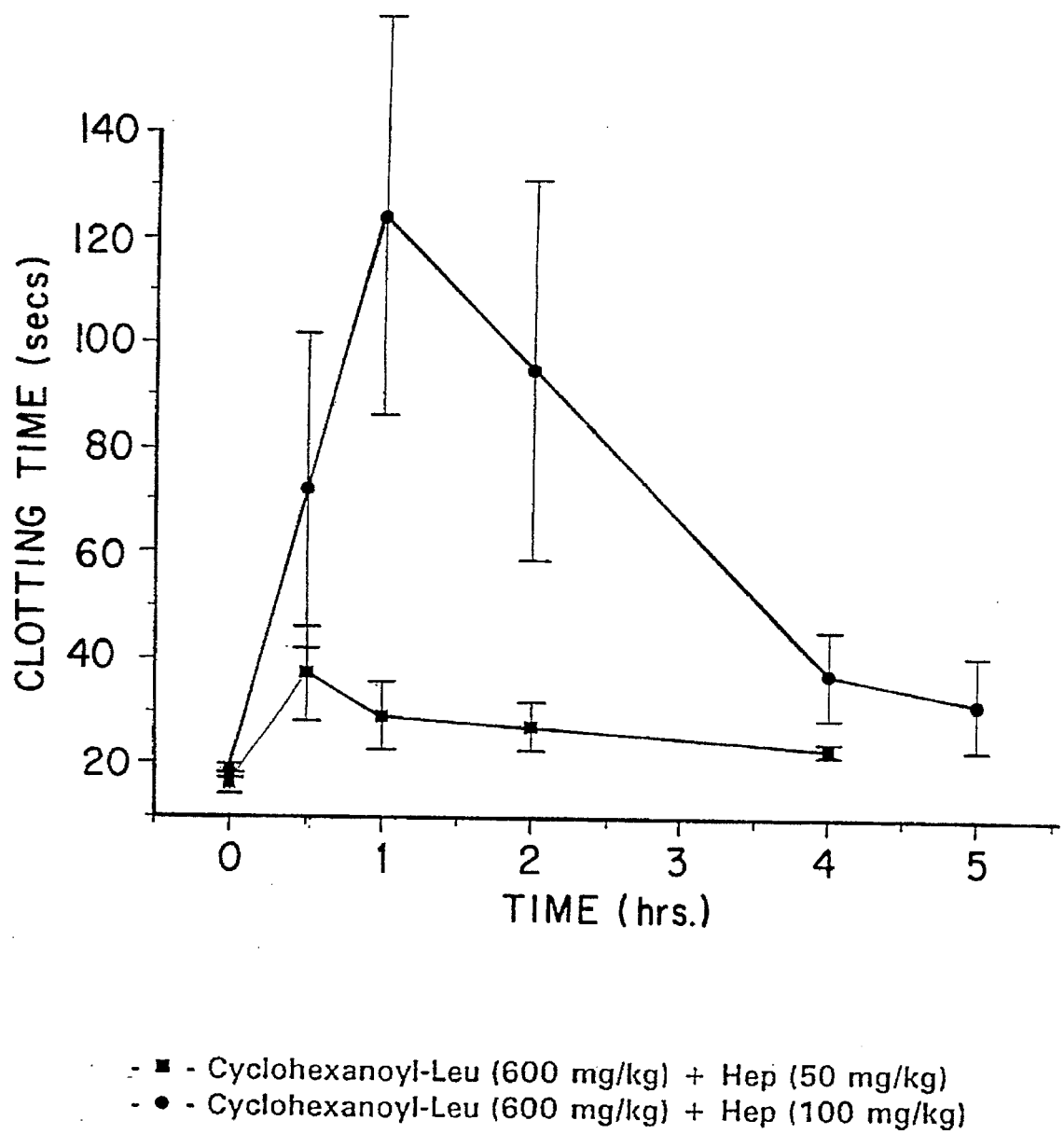

Two samples were prepared, having 600 mg/kg of cyclohexanoyl-(L)-leucine and 50 mg/kg of heparin and 600 mg/kg of cyclohexanoyl-(L)-leucine and 100 mg/kg of heparin, respectively. The samples were given to fasted rats as described in Example 13. The results of the test are illustrated in FIG. 7.

Example 15

Figure 8:
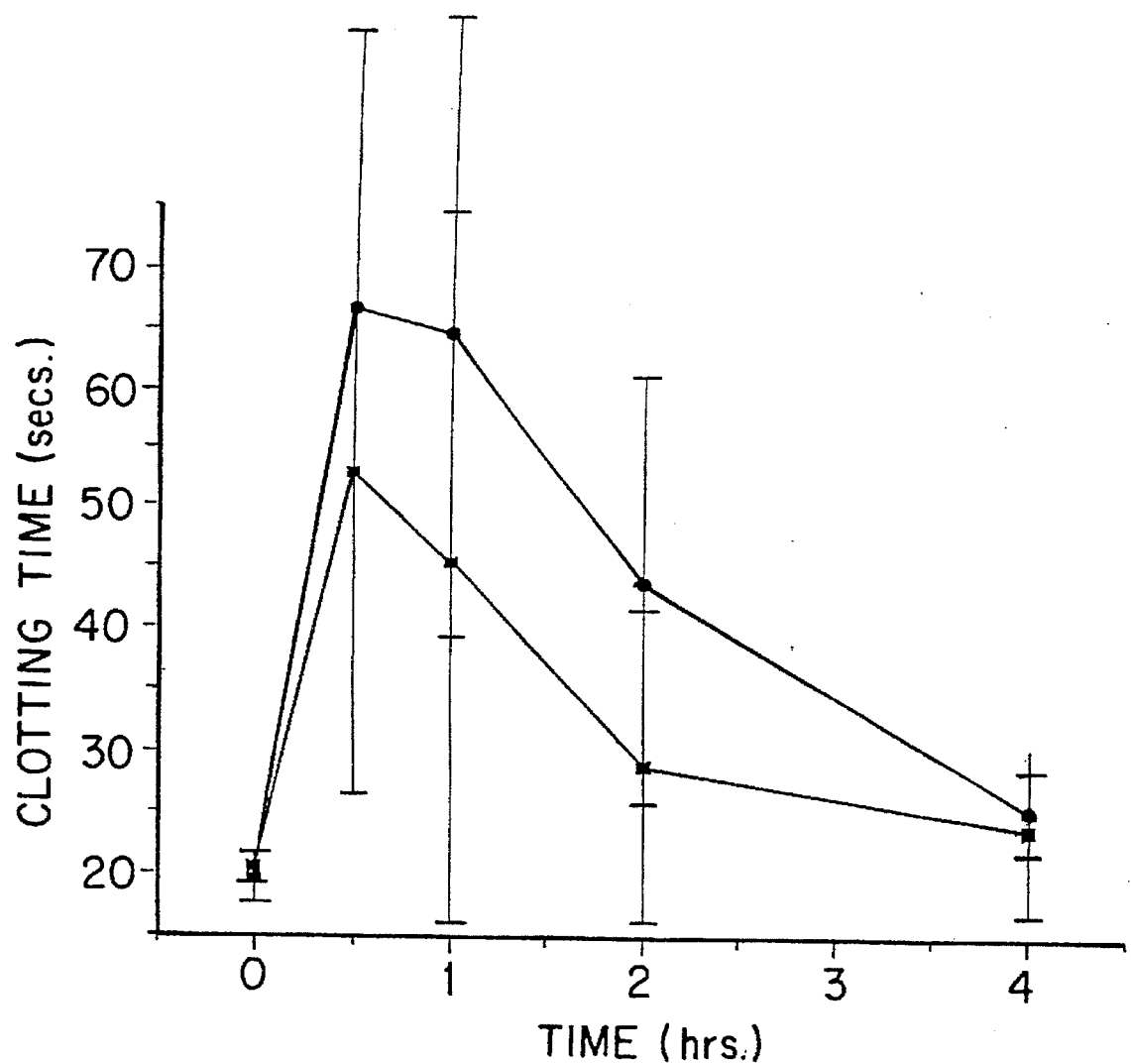
FIG. 8 is a graphic illustration of the results of oral gavage testing in rats using heparin with cyclohexanoyl-(L)-arginine carrier.

Two samples were prepared, having 100 mg/kg of cyclohexanoyl-(L)-arginine and 100 mg/kg of heparin and 600 mg/kg of cyclohexanoyl-(L)-arginine and 100 mg/kg of heparin, respectively. The samples were given to fasted rats as described in Example 12. The results of the test are illustrated in FIG. 8.

Example 16

Figure 9:
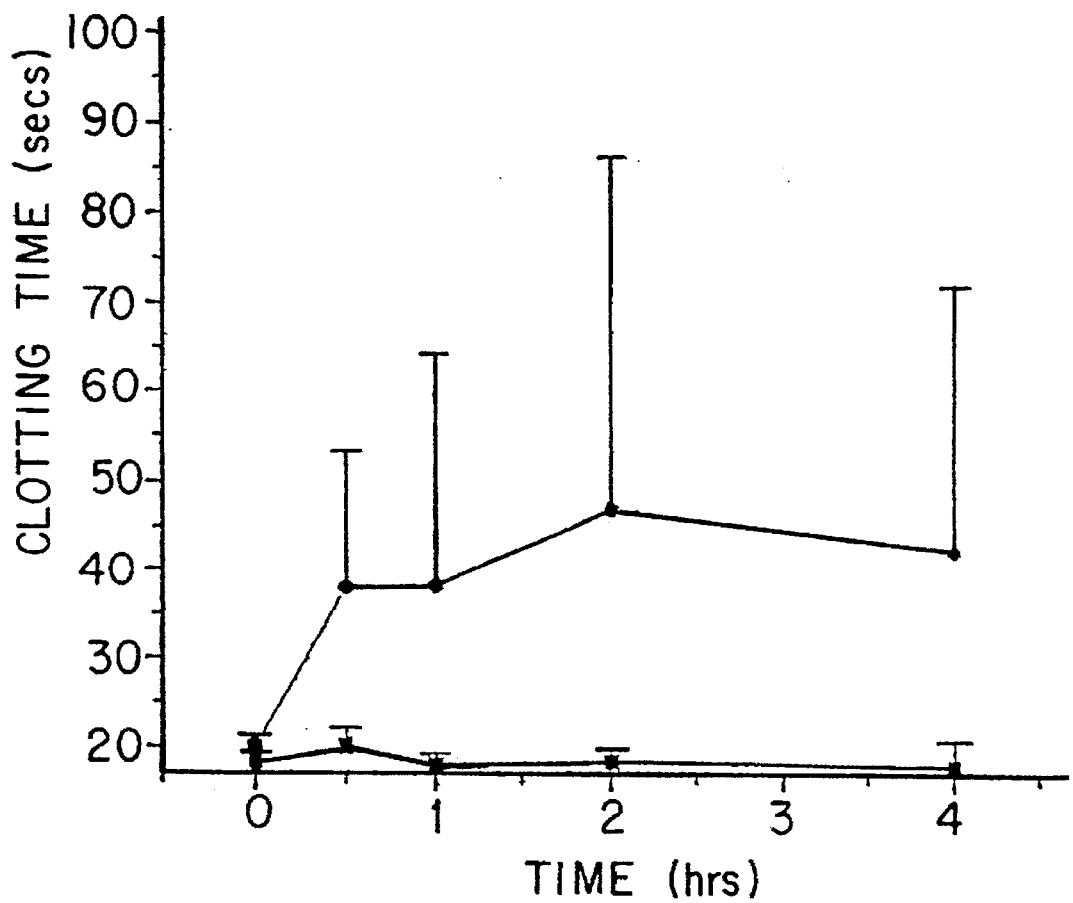
FIGS. 9 and 10 are graphic illustrations of the results of intraduodenal injection testing in rats using heparin with cyclohexanoyl-(L)-leucine carrier.

A sample having 300 mg/kg of cyclohexanoyl-(L)-leucine and 25 mg/kg of heparin was prepared. The sample was given to rats by intraduodenal injection. As a comparison heparin, at a dose of 25 mg/kg was administered by intraduodenal injection. The results of the test are illustrated graphically in FIG. 9.

Example 17

Figure 10:
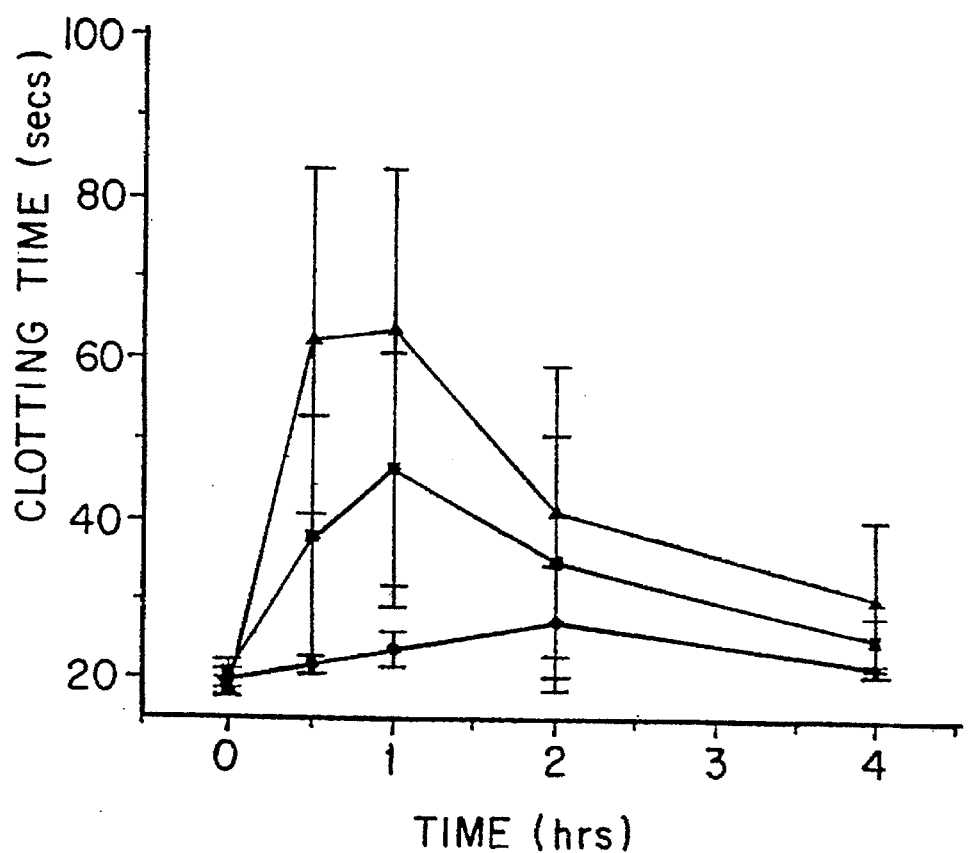

A sample having 300 mg/kg of cyclohexanoyl-(L)-leucine and 50 mg/kg of heparin was prepared. The sample was given to rats by intraduodenal injection. As a comparison cyclohexanoyl-(L)-leucine without any heparin was administered by intraduodenal injection. After 30 minutes this was followed by a dose of heparin, 50 mg/kg administered by intraduodenal injection. A second comparison, a dose of heparin alone, 50 mg/kg, was also administered by intraduodenal injection. The results of the test are illustrated graphically in FIG. 10.

EXAMPLE 18

PREPARATION OF LOW MOLECULAR WEIGHT HEPARIN SAMPLES

Samples containing low molecular weight heparin were prepared as described in Example 12.

Example 19

LOW MOLECULAR WEIGHT HEPARIN In Vivo EXPERIMENTS IN RATS

Figure 11:
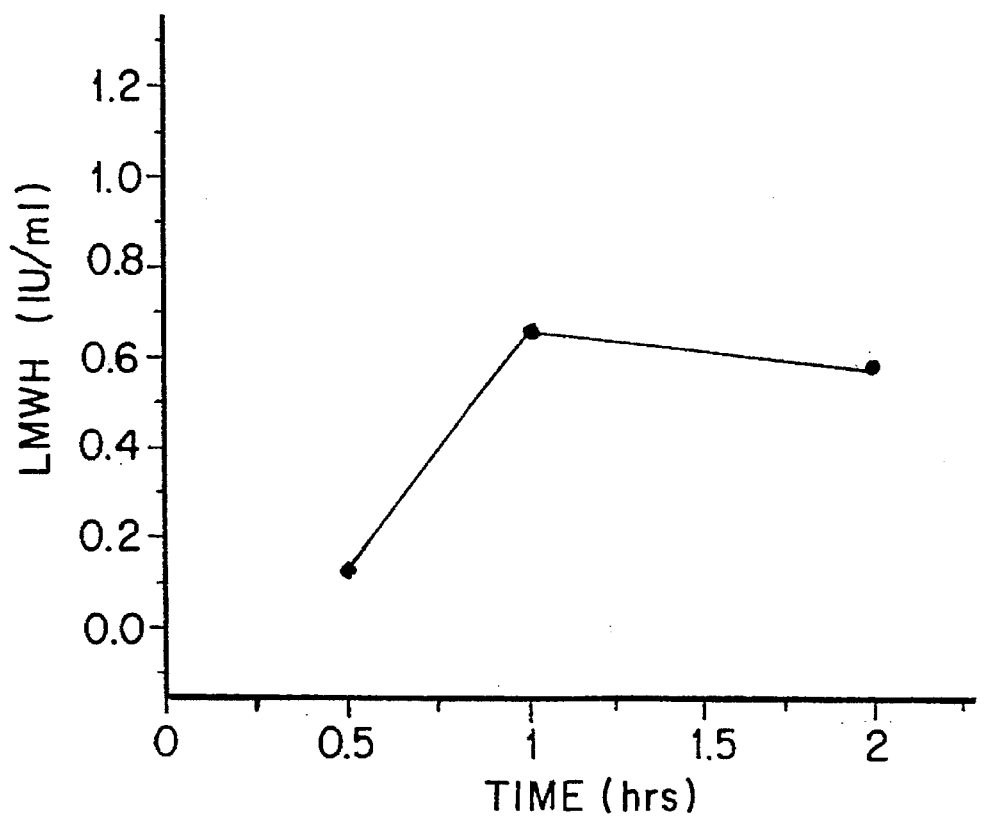
FIGS. 11 and 12 are graphic illustrations of the results of oral gavage testing in rats using low molecular weight heparin with cyclohexanoyl-(L)-leucine carrier.

Samples containing low molecular weight heparin (LMWH) and cyclohexanoyl-(L)-leucine as described in Example 19 were prepared and administered, by oral gavage, to a group of fasted rats. Blood samples were collected serially from the tail artery. Low molecular weight heparin (LMWH) was determined in plasma samples. The plasma level was measured with an antiFactor Xa assay kit available from Chromogenix A. B., Sweden. The results of the test are illustrated in FIG. 11.

Example 20

Figure 12:
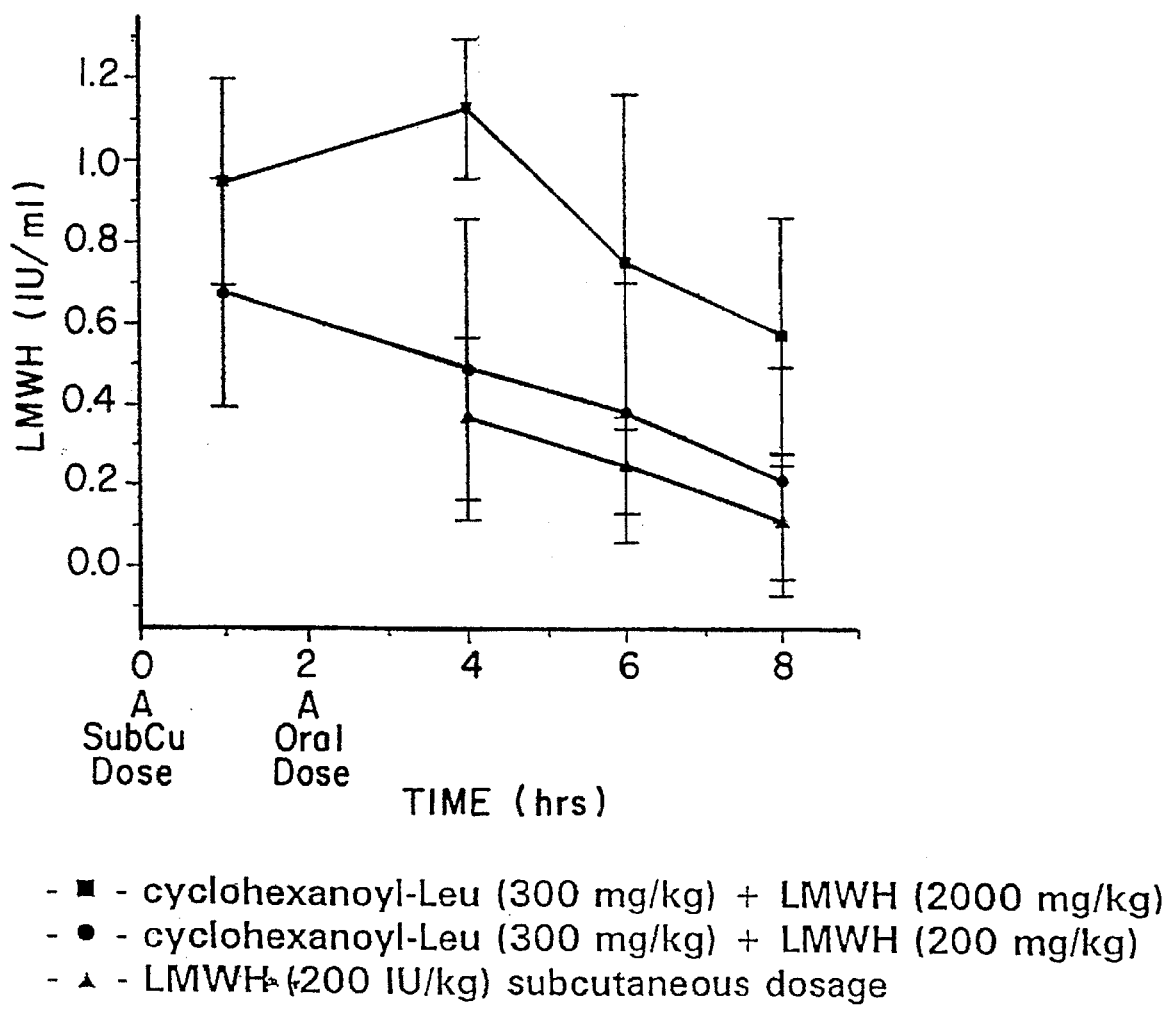

A sample having 300 mg/kg of cyclohexanoyl-(L)-leucine and 8000 IU/kg low molecular weight heparin was prepared. The sample was given to fasted rats as described in Example 20. The results of the test are illustrated in FIG. 12.

In Vivo EVALUATION OF CROMOGLYCOLATE PREPARATIONS IN RATS

Example 21

Figure 13:
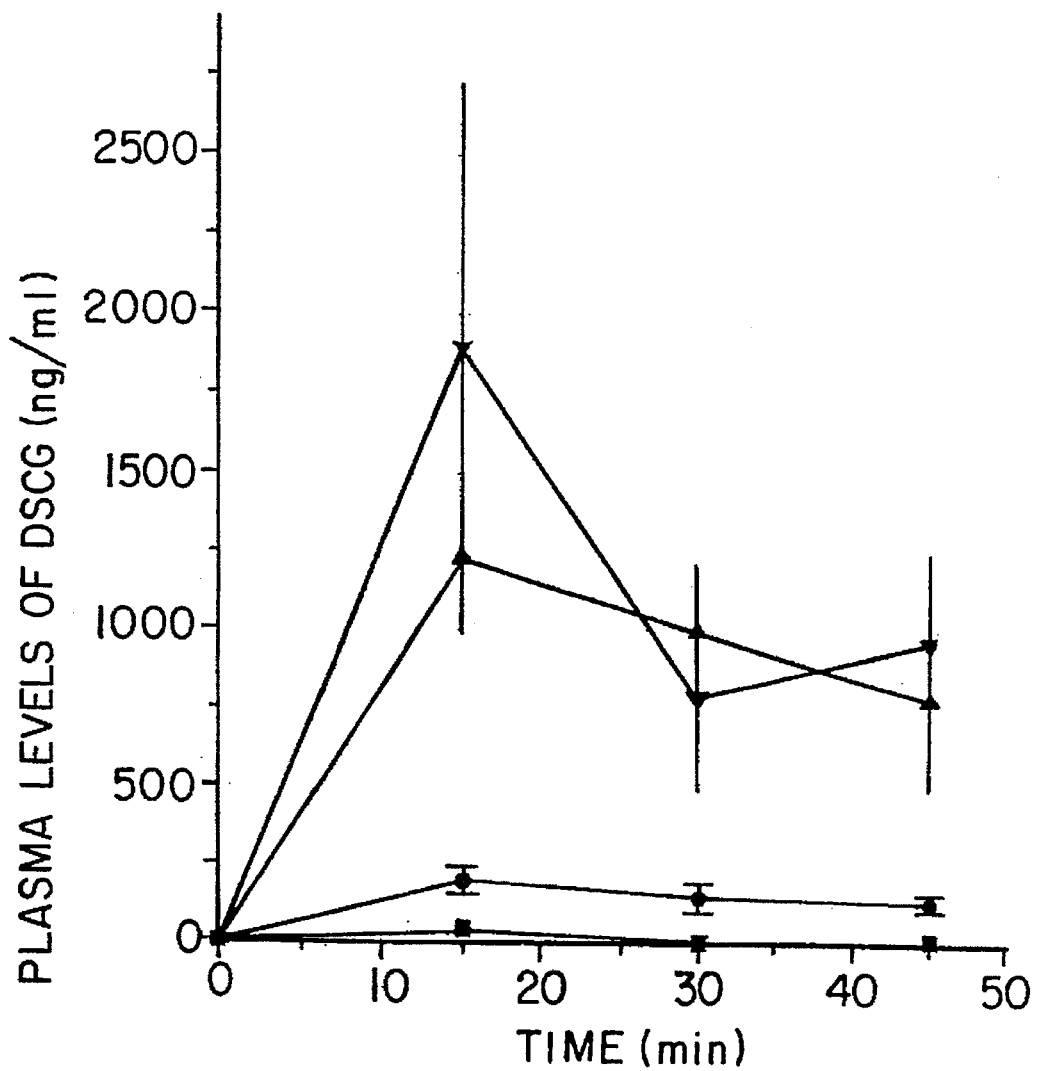
FIG. 13 is a graphic illustration of the results of oral gavage testing in rats using disodium cromoglycate with cyclohexanoyl-(L)-leucine carrier.

Following the procedures described herein samples containing the carriers of the subject invention and disodium cromoglycolate were prepared. The sample, in 0.85N citric acid and 0.5% acacia, contained 400 mg/kg of cyclohexanoyl-(L)-leucine and 50 mg/kg of disodium cromoglycate (DSCG). The pH of this sample was 7.1. A second sample was prepared at a pH of 4.6. The animals were administered the samples by oral gavage. As a comparison the DSCG was delivered in water, pH 7.2, and in citric acid, pH 3.7. The delivery was evaluated by using the procedure described by A. Yoshimi in *Pharmcobio-Dyn.*, 15, pages 681–686, (1992). The results of the tests are illustrated in FIG. 13.

In Vivo EVALUATION OF INTERFERON PREPARATIONS IN RATS

Example 22

Following the procedures described herein samples containing the carriers of the subject invention, in a Trizma® hydrochloride buffer solution (Tris-HCl) at a pH of about 7-8, and interferon α2b were prepared. The animals were administered the drug by oral gavage. The delivery was evaluated by using an ELISA assay for human interferon α.

Figure 14:
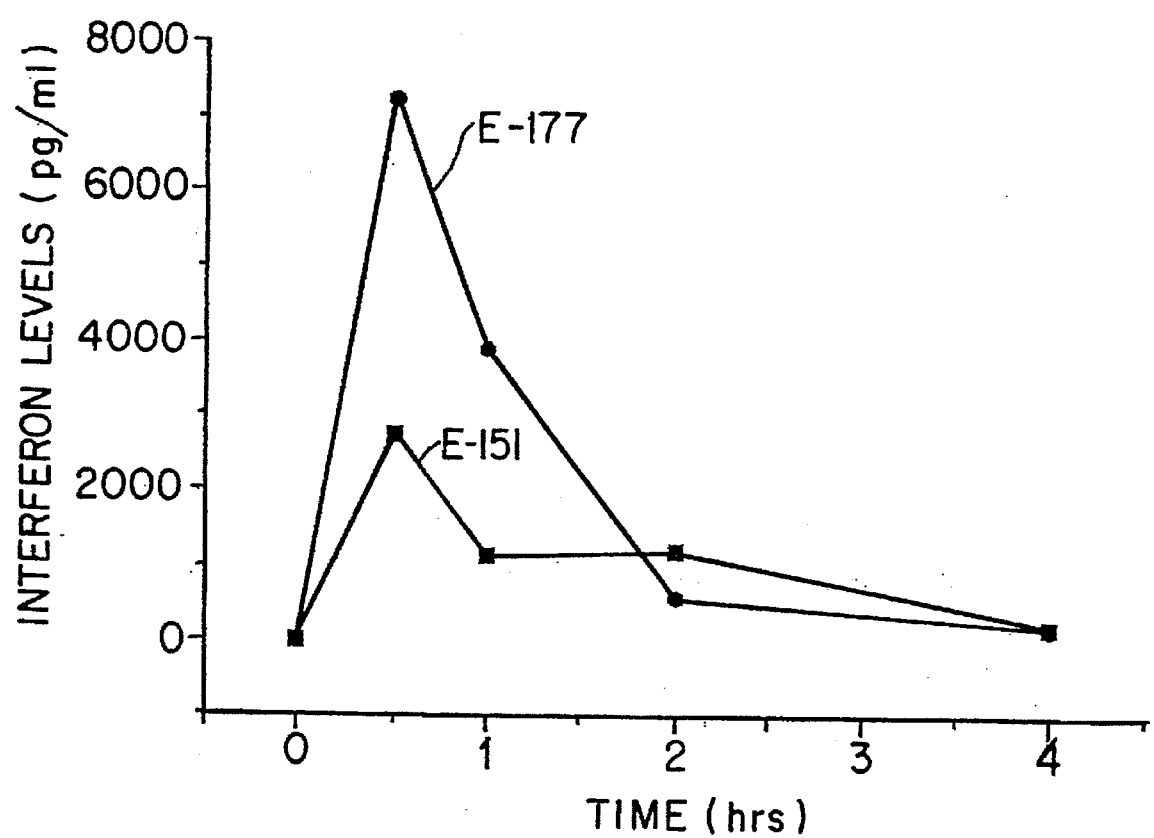
FIG. 14 is a graphic illustration of the results of oral gavage testing in rats using interferon α2b (rhIFN) with cyclohexanoyl-(L)-phenylglycine and cyclohexanoyl-(L)-arginine carriers.

Two samples having 800 mg/kg of cyclohexanoyl-(L)-phenylglycine in a buffered solution and 1000µg/kg of interferon α2b and 800 mg/kg cyclohexanoyl-(L)-arginine in a buffered solution and 1000µg/kg of interferon α2b were prepared. The samples were given to fasted rats by oral gavage. The results of the test are illustrated in FIG. 14.

Example 23

Figure 15:
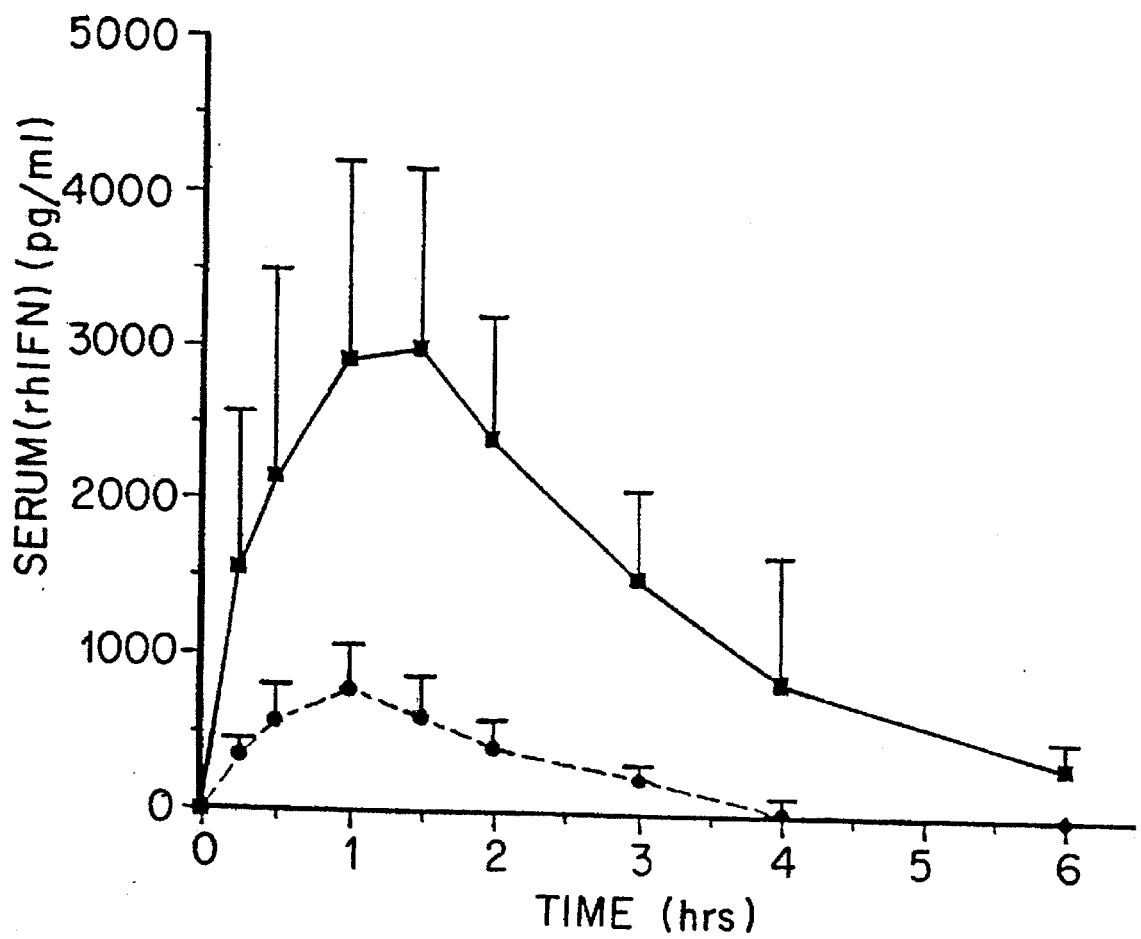
FIG. 15 is a graphic illustration of the results of oral administration testing in monkeys using interferon α2b with cyclohexanoyl-phenylene and cyclohexanoyl-arginine carriers.

Two samples having 800 mg/kg of cyclohexanoyl-(L)-phenylglycine in a buffered solution and 1000µg/kg of interferon α2b and cyclohexanoyl-(L)-arginine in a buffered solution and 1000µg/kg of interferon α2b were prepared. The samples were orally administered to monkeys. The results of the test are illustrated in FIG. 15.

Example 24

Figure 16:
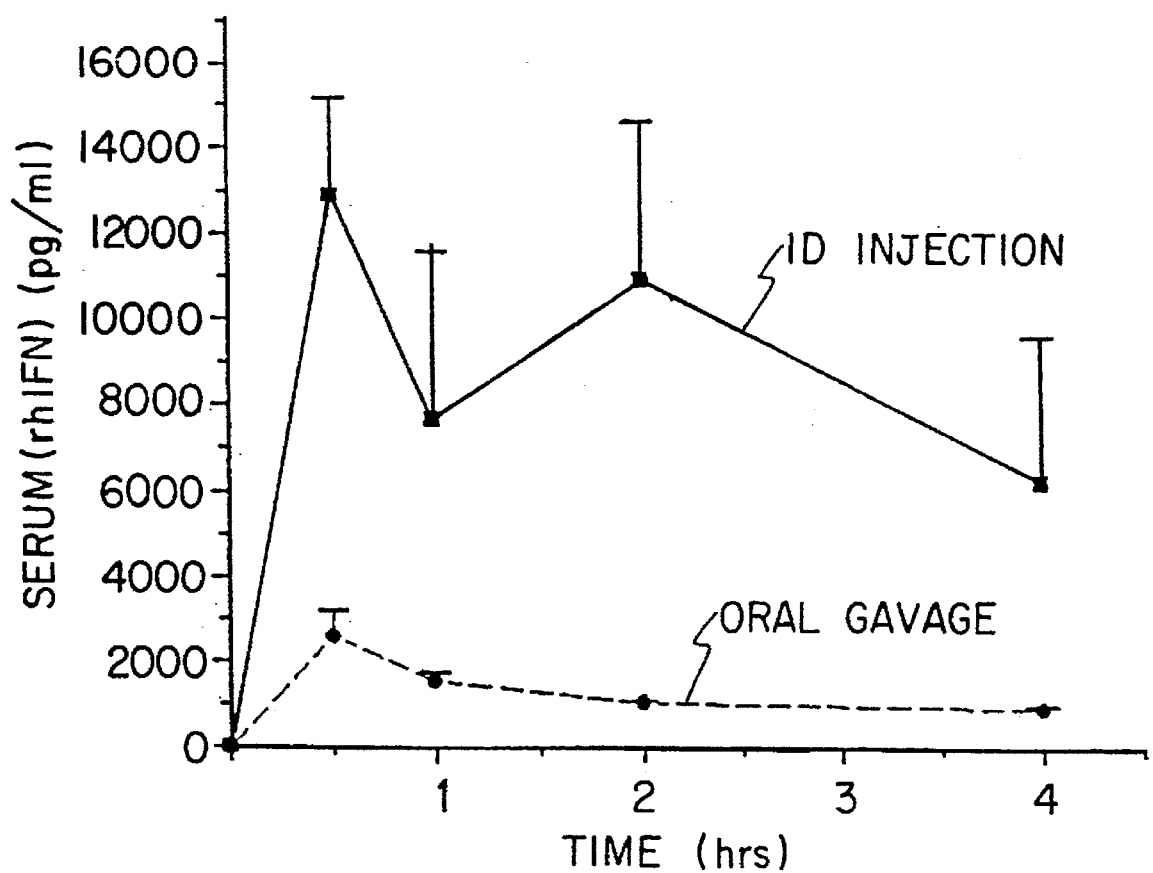
FIG. 16 is a graphic illustration of the results of oral gavage and intraduodenal injection testing in rats using interferon α2b and cyclohexanoyl-(L)-phenylglycine carrier.

A sample having 400 mg/kg of cyclohexanoyl-(L)-phenylglycine in a buffered solution and 500µg/kg of interferon α2b was prepared. The sample was given to fasted rats by oral gavage. The sample was also given to a second group of rats by intraduodenal injection. The results of the test are illustrated in FIG. 16.

Example 25

Figure 17:
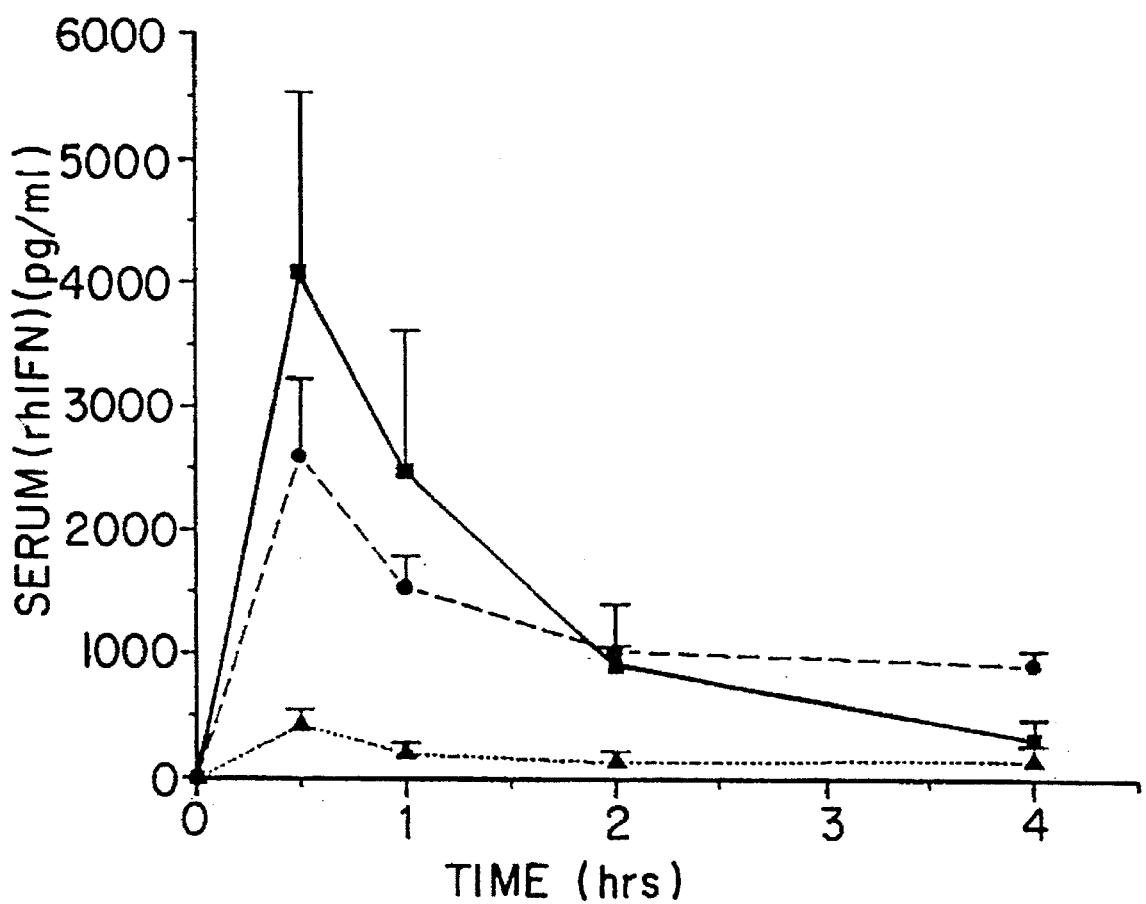
FIG. 17 is a graphic illustration of the results of oral gavage testing in rats using interferon α2b and cyclohexanoyl-(L)-phenylglycine carrier.

Three samples having 400 mg/kg of cyclohexanoyl-(L)-phenylglycine in a buffered solution with 1000µg/kg of interferon α2b, 500µg/kg of interferon α2b and 250µg/kg of interferon α2b were prepared. The samples were given to fasted rats by oral gavage. The results of the test are illustrated in FIG. 17.

All patents, patent applications, literature publications and test methods cited herein are hereby incorporated by reference.

Many variations of the present invention will suggest themselves to those skilled in the art in light of the above detailed disclosure. All such modifications are within the full intended scope of the appended claims.

What is claimed is:

1. A composition comprising:
   (A) at least one biologically active agent selected from the group consisting of a peptide, a mucopoly-saccharide, a carbohydrate, a lipid, a pesticide, or any combination thereof, and
   (B)
   (a) at least one acylated amino acid;
   (b) at least one peptide comprising at least one acylated amino acid; or
   (c) a combination of (a) and (b);
   wherein said acylated amino acid is acylated by a $C_3$–$C_{10}$ cycloalkyl acylating agent.

2. The composition according to claim 1, wherein said amino acid has the formula

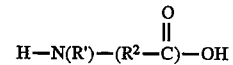

wherein:

$R^1$ is hydrogen, $C_1$–$C_4$ alkyl, or $C_2$–$C_4$ alkenyl;

$R^2$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl)phenyl, ($C_1$–$C_{10}$ alkyl) naphthyl, ($C_2$–$C_{10}$ alkenyl)naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkenyl);

$R^2$ being optionally substituted with $C_1$–$C_4$ alkyl, $C_2$–$C_4$ alkenyl, $C_1$–$C_4$ alkoxy, —OH, —SH, —$CO_2R^3$, $C_3$–$C_{10}$ cycloalkyl, $C_3$–$C_{10}$ cycloalkenyl, heterocycle having 3–10 ring atoms wherein the hetero atom is one or more of N, O, S, or any combination thereof, aryl, ($C_1$–$C_{10}$ alk)aryl, ar($C_1$–$C_{10}$ alkyl), or any combination thereof;

$R^2$ being optionally interrupted by oxygen, nitrogen, sulfur, or any combination thereof; and $R^3$ is hydrogen, $C_1$–$C_4$ alkyl, or $C_2$–$C_4$ alkenyl.

3. The composition according to claim 1, wherein said acylated amino acid has the formula

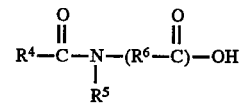

wherein:

$R^4$ is $C_3$–$C_{10}$ cycloalky;

$R^5$ hydrogen, $C_1$–$C_4$ alkyl, or $C_2$–$C_4$ alkenyl;

$R_6$ is $C_1$–$C_{24}$ alkyl, $C_2$–$C_{24}$ alkenyl, $C_3$–$C_{10}$ cycloalky, $C_3$–$C_{10}$ cycloalkenyl, phenyl, naphthyl, ($C_1$–$C_{10}$ alkyl) phenyl, ($C_2$–$C_{10}$ alkenyl)phenyl, ($C_2$–$C_{10}$ alkyl) naphthyl, ($C_2$–$C_{10}$ alkenyl)naphthyl, phenyl ($C_1$–$C_{10}$ alkyl), phenyl ($C_2$–$C_{10}$ alkenyl), naphthyl($C_1$–$C_{10}$ alkyl), or naphthyl ($C_2$–$C_{10}$ alkenyl);

$R_6$ being optionally substituted with $C_1$–$C_4$ alkyl, $C_2$–$C_4$ alkenyl, $C_1$–$C_4$ alkoxy, —OH, —SH, —$CO_2R^7$, $C_3$–$C_7$ cycloalkyl, $C_3$–$C_7$ cycloalkenyl, heterocycle having 3–10 ring atoms wherein the hereto atom is one or more atom of N, O, S or any combination thereof, aryl, ($C_1$–$C_{10}$ alk)aryl, ar($C_1$–$C_{10}$ alkyl) or any combination thereof; and $R^6$ being optionally interrupted by oxygen, nitrogen, sulfur, or any combination thereof.

4. A composition comprising:
(A) at least one biologically active agent selected from the group consisting of human growth hormone, bovine growth hormone, growth hormone-releasing hormone, an interferon, interleukin-II insulin, heparin, calcitonin, erythropoietin, atrial naturetic factor, a monoclonal antibody, somatostatin, adrenocorticotropin, gonadotropin releasing hormone, oxytocin, vasopressin, cromolyn sodium, vancomycin, desferrioxamine (DFO), or any combination therof, and
(B)
(a) at least one acylated amino acid;
(b) at least one peptide comprising at least one acylated amino acid; or
(c) a combination of (a) and (b);
wherein said acylated amino acid is acylated by
a $C_3$–$C_{10}$ cycloalkyl acylating agent.

5. The composition according to claim 4, wherein said biologically-active agent is selected from the group consisting of an interferon, interleukin-II, insulin, heparin, calcitonin, oxytocin, vasopressin, cromolyn sodium, vancomycin, DFO or any combination thereof.

6. The composition according to claim 5, wherein said biologically-active agent is calcitonin.

7. The composition according to claim 1, wherein said amino acid is a naturally occurring amino acid.

8. The composition according to claim 1, wherein said amino acid is a synthetic amino acid.

9. The composition according to claim 1, wherein said amino acid is an α-amino acid.

10. The composition according to claim 1, wherein said amino acid is a non-α-amino acid.

11. The composition according to claim 2, wherein said amino acid is selected from the group consisting of alanine, arginine, asparagine, aspartic acid, citrulline, cysteine, cystine, glutamine, glycine, histidine, isoleucine, leucine, lysine, methionine, ornithine, phenylalanine, phenylglycine, proline, serine, threonine, tryptophan tyrosine, valine, hydroxyproline, γ-carboxyglutamate, O-phosphoserine, β-alanine, α-aminobutyric acid, γ-aminobutyric acid, α-aminoisobutyric acid, 4-(4-aminophenyl)butyric acid, (aminophenyl)acetic acid, aminobenzoic acid, 4-aminohippuric acid, (aminomethyl)benzoic acid ε-aminocaproic acid, 7-aminoheptanoic acid, β-aspartic acid, γ-glutamic acid, cysteine(ACM), ε-lysine, ε-lysine (A-Fmoc), methionine sulfone, norleucine, norvaline, ornithine, d-ornithine, p-nitro-phenylalanine, hydroxy proline, and thioproline.

12. The composition according to claim 11, wherein said amino acid is selected from the group consisting of arginine, leucine, lysine, phenylalanine, tyrosine, valine, phenylglycine, 4-(4-aminophenyl)butyric acid, 4-(4-aminophenyl)acetic acid and aminobenzoic acid.

13. The composition according to claim 1, wherein said peptide is selected from the group consisting of a di-peptide, a tri-peptide, a tetra-peptide, or a penta-peptide.

14. The composition according to claim 13, wherein said peptide comprises at least one naturally occurring amino acid.

15. The composition according to claim 13, wherein said peptide comprises at least one synthetic amino acid.

16. The composition according to claim 13, wherein said peptide comprises at least one α-amino acid.

17. The composition according to claim 13, wherein said peptide comprises one or more amino acids selected from the group consisting of alanine, arginine, asparagine, aspartic acid, citrulline, cysteine, cystine, glutamine, glycine, histidine, isoleucine, leucine, lysine, methionine, ornithine, phenylalanine, phenylglycine, proline, serine, threonine, tryptophan tyrosine, valine, hydroxy proline, γ-carboxyglutamate, O-phosphoserine, β-alanine, α-amino butyric acid, γ-amino butyric acid, α-amino isobutyric acid, ε-amino caproic acid, 7-amino heptanoic acid, β-aspartic acid, ε-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, and thioproline.

18. The composition according to claim 17, wherein said peptide is formed from one or more amino acids selected from the group consisting of arginine, leucine, lysine, phenylalanine, tyrosine, valine, and phenylglycine.

19. The composition according to claim 1, wherein said acylating agent has the formula

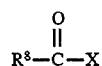

wherein
$R^1$ is
$C_3$–$C_{10}$ cycloalkyl; and
X is a leaving group.

20. The composition according to claim 19, wherein $R^8$ is cyclohexyl, cyclopentyl, cyclopropyl, or cycloheptyl.

21. The composition according to claim 1, wherein component (b)(i) comprises a mixture of two or more acylated amino acids.

22. The composition according to claim 1, comprising a microsphere.

23. A dosage unit form comprising
(A) a composition according to claim 1; and
(B)
(a) an excipient,
(b) a diluent,
(c) a disintegrant,
(d) a lubricant,
(e) a plasticizer,
(f) a colorant, or
(g) any combination thereof.

24. A dosage unit form according to claim 23 comprising a tablet, a capsule, or a liquid.

25. A method for administering a biologically-active agent to an animal in need of said agent, said method comprising administering orally to said animal a composition as defined in claim 1.

26. A method for preparing a composition, said method comprising mixing:
(A) at least one biologically-active agent selected from the group consisting of a peptide, a mucopolysaccharide, a carbohydrate, a lipid, a pesticide, or any combination thereof;
(B)
(a) at least one acylated amino acid;
(b) at least one peptide comprising at least one acylated amino acid; or
(c) a combination of (a) and (b);
wherein said acylated amino acid is acylated by
a $C_3$–$C_{10}$ cycloalkyl acylating agent; and
(C) optionally a dosing vehicle.

27. The method according to claim 26, further comprising a stabilizing additive.

28. The method according to claim 27, wherein the stabilizing additive is selected from the group consisting of gum acacia, gelatin, polyethylene glycol or polylysine.

29. The composition according to claim 1, wherein said biologically active agent comprises an antigen.

* * * * *